(12) United States Patent
Qiao et al.

(10) Patent No.: US 9,045,383 B2
(45) Date of Patent: Jun. 2, 2015

(54) REDUCTIVE BIOMASS LIQUEFACTION

(71) Applicant: Virent, Inc., Madison, WI (US)

(72) Inventors: Ming Qiao, Pewaukee, WI (US); Randy D. Cortright, Madison, WI (US); John Kania, Madison, WI (US); Elizabeth Woods, Middleton, WI (US)

(73) Assignee: Virent, Inc., Madison, WI (US)

( * ) Notice: Subject to any disclaimer, the term of this patent is extended or adjusted under 35 U.S.C. 154(b) by 19 days.

(21) Appl. No.: 14/133,996

(22) Filed: Dec. 19, 2013

(65) Prior Publication Data

US 2014/0107353 A1 Apr. 17, 2014

Related U.S. Application Data

(62) Division of application No. 13/339,994, filed on Dec. 29, 2011, now Pat. No. 8,642,813.

(60) Provisional application No. 61/428,461, filed on Dec. 30, 2010, provisional application No. 61/481,551, filed on May 2, 2011.

(51) Int. Cl.
*C07B 63/00* (2006.01)
*B01J 20/34* (2006.01)
*C07C 29/132* (2006.01)
(Continued)

(52) U.S. Cl.
CPC .............. *C07B 63/00* (2013.01); *B01J 20/34* (2013.01); *C07C 29/132* (2013.01); *B01J 23/462* (2013.01); *B01J 23/464* (2013.01); *B01J 23/6527* (2013.01); *B01J 23/687* (2013.01); *C10G 1/06* (2013.01); *C10G 1/065* (2013.01); *C10G 3/42* (2013.01); *C10G 3/47* (2013.01); *C10G 2300/1011* (2013.01); *C10G 2300/805* (2013.01); *C10G 2400/30* (2013.01); *C10G 2300/44* (2013.01); *C10G 2300/1014* (2013.01)

(58) Field of Classification Search
None
See application file for complete search history.

(56) References Cited

U.S. PATENT DOCUMENTS 2,220,624 A 11/1940 Sherrard
5,675,048 A 10/1997 Zhang et al.
(Continued)

FOREIGN PATENT DOCUMENTS

GB 1165141 9/1969
WO 2008109877 A1 9/2008

OTHER PUBLICATIONS

Fukuoka, et al., Catalytic Conversion of Cellulose into Sugar Alcohols, Angew. Chem., 2006, 118:5285-5287.
(Continued)

*Primary Examiner* — Melvin C Mayes
*Assistant Examiner* — Sheng H Davis
(74) *Attorney, Agent, or Firm* — Quarles & Brady LLP

(57) ABSTRACT

The present invention provides methods, reactor systems, and catalysts for converting in a continuous process biomass to less complex oxygenated compounds for use in downstream processes to produce biofuels and chemicals. The invention includes methods of converting the components of biomass, such as hemicellulose, cellulose and lignin, to water-soluble materials, including lignocellulosic derivatives, cellulosic derivatives, hemicellulosic derivatives, carbohydrates, starches, polysaccharides, disaccharides, monosaccharides, sugars, sugar alcohols, alditols, polyols, diols, alcohols, ketones, cyclic ethers, esters, carboxylic acids, aldehydes, and mixtures thereof, using hydrogen and a heterogeneous liquefaction catalyst.

20 Claims, 10 Drawing Sheets

(51) Int. Cl.
    *B01J 23/46*      (2006.01)
    *B01J 23/652*      (2006.01)
    *B01J 23/68*      (2006.01)
    *C10G 1/06*      (2006.01)
    *C10G 3/00*      (2006.01)

(56) References Cited

U.S. PATENT DOCUMENTS

| | | |
|---|---|---|
| 5,986,158 A | 11/1999 | Van Broekhoven et al. |
| 6,699,457 B2 | 3/2004 | Cortright et al. |
| 6,953,873 B2 | 10/2005 | Cortright et al. |
| 6,964,757 B2 | 11/2005 | Cortright et al. |
| 7,767,867 B2 | 8/2010 | Cortright |
| 7,977,517 B2 | 7/2011 | Cortright et al. |
| 8,017,818 B2 | 9/2011 | Cortright et al. |
| 8,053,615 B2 | 11/2011 | Cortright et al. |
| 8,105,968 B2 | 1/2012 | Gaffney et al. |
| 2008/0025903 A1 | 1/2008 | Cortright |
| 2008/0072478 A1 | 3/2008 | Cooper |
| 2008/0300434 A1 | 12/2008 | Cortright et al. |
| 2009/0211942 A1 | 8/2009 | Cortright et al. |
| 2009/0218061 A1 | 9/2009 | Schinski et al. |
| 2010/0076233 A1 | 3/2010 | Cortright et al. |
| 2010/0228062 A1 | 9/2010 | Babicki et al. |
| 2010/0256428 A1 | 10/2010 | Marker et al. |

OTHER PUBLICATIONS

Kobayashi, et al., Water-Tolerant Mesoporous-Carbon-Supported Ruthenium Catalysts for the Hydrolysis of Cellulose to Glucose, ChemSusChem, 2010, 3:440-443.

PCT International Search Report and Written Opinion, PCT/US2011/067816, Mar. 21, 2012, 13 pages.

Figure 4. Liquefaction of Loblolly Pine

Figure 5. Liquefaction of Loblolly Pine Product Selectivity

Figure 6. Liquefaction of Corn Cob Product Selectivity

Figure 7. Liquefaction of MCC

Figure 8. Liquefaction of MCC Product Selectivity

Overall Balances and Biomass Conversions Results of Loblolly Pine Deconstruction at Varying Temperature and Pressures Overall Biomass Conversions Results of Loblolly Pine Deconstruction at Varying Temperature and Pressures

REDUCTIVE BIOMASS LIQUEFACTION

CROSS-REFERENCE TO RELATED APPLICATIONS

This application is a divisional of U.S. patent application Ser. No. 13/339,994 filed on Dec. 29, 2011, now U.S. Pat. No. 8,642,813, which claims the benefit of U.S. Provisional Application Nos. 61/428,461 filed on Dec. 30, 2010 and 61/481,551 filed on May 2, 2011. Each of these applications is incorporated by reference herein.

FEDERAL FUNDING STATEMENT

This invention was made with government support under award No. 70NANB7H7023, requisition No. 4700558 awarded by NIST through the ATP program. The government has certain rights in the invention.

TECHNICAL FIELD

The present invention is directed to catalysts and methods for liquefying and fractionating biomass using heterogeneous catalysts.

BACKGROUND OF THE INVENTION

The increasing cost of fossil fuel and environmental concerns have stimulated worldwide interest in developing alternatives to petroleum-based fuels, chemicals, and other products. Biomass materials are one possible renewable alternative.

Lignocellulosic biomass includes three major components. Cellulose, a primary sugar source for bioconversion processes, includes high molecular weight polymers formed of tightly linked glucose monomers. Hemicellulose, a secondary sugar source, includes shorter polymers formed of various sugars. Lignin includes phenylpropanoic acid moieties polymerized in a complex three dimensional structure. The resulting composition of lignocellulosic biomass is roughly 40-50% cellulose, 20-25% hemicellulose, and 25-35% lignin, by weight percent.

No cost-effective process currently exists for efficiently converting the primary components of biomass, including lignin, to compounds better suited for producing fuels, chemicals, and other products. This is generally because each of the lignin, cellulose and hemicellulose components demand distinct processing conditions, such as temperature, pressure, catalysts, reaction time, etc. in order to effectively break apart its polymer structure. Because of this distinctness, most processes are only able to convert specific fractions of the biomass, such as the cellulose and hemicellulose components, leaving the remaining components behind for additional processing or alternative uses.

Existing methods for converting biomass to usable feedstock are also not sufficient to meet the growing needs. Hot water extraction of hemicelluloses from biomass has been well documented, but the sugars produced by hot water extraction are unstable at high temperatures leading to undesirable decomposition products. Therefore, the temperature range of the water used for hot water extraction is limited, which can reduce the effectiveness of the hot water extraction.

Studies have also shown that it is possible to convert microcrystalline cellulose (MCC) to polyols using hot, compressed water and a hydrogenation catalyst (Fukuoka & Dhepe, 2006; Luo et al., 2007; and Yan et al., 2006). Typical hydrogenation catalysts include ruthenium or platinum supported on carbon or aluminum oxide. However, these studies also show that only low levels of MCC are converted with these catalysts. Selectivity toward desired sugar alcohols is also low. Therefore, a process for converting biomass to polyols for further processing to fuels, chemicals, and other products would be beneficial.

Recent attention has been placed on processes that make use of heterogeneous catalysts to produce liquid fuels and chemicals from biomass. Such processes have the added benefit of being feedstock flexible, continuous and more readily scalable than biological systems involving batch processing. Aqueous-phase reforming (APR) and hydrodeoxygenation (HDO) are catalytic reforming processes that can generate hydrogen, hydrocarbons and other oxygenated molecules from oxygenated hydrocarbons derived from a wide array of biomass. The oxygenated hydrocarbons include starches, mono- and poly-saccharides, sugars, sugar alcohols, etc. Various APR methods and techniques are described in U.S. Pat. Nos. 6,699,457; 6,964,757; 6,964,758; and 7,618,612 (all to Cortright et al., and entitled "Low-Temperature Hydrogen Production from Oxygenated Hydrocarbons"); U.S. Pat. No. 6,953,873 (to Cortright et al., and entitled "Low-Temperature Hydrocarbon Production from Oxygenated Hydrocarbons"); and U.S. Pat. Nos. 7,767,867 and 7,989,664 and U.S. Application Ser. No. 2011/0306804 (all to Cortright, and entitled "Methods and Systems for Generating Polyols"). Various APR and HDO methods and techniques are described in U.S. Patent Application Ser. Nos. 2008/0216391; 2008/0300434; and 2008/0300435 (all to Cortright and Blommel, and entitled "Synthesis of Liquid Fuels and Chemicals from Oxygenated Hydrocarbons"); U.S. Patent Application Ser. No. 2009/0211942 (to Cortright, and entitled "Catalysts and Methods for Reforming Oxygenated Compounds"); U.S. Patent Application Ser. No. 2010/0076233 (to Cortright et al., and entitled "Synthesis of Liquid Fuels from Biomass"); International Patent Application No. PCT/US2008/056330 (to Cortright and Blommel, and entitled "Synthesis of Liquid Fuels and Chemicals from Oxygenated Hydrocarbons"); and commonly owned co-pending International Patent Application No. PCT/US2006/048030 (to Cortright et al., and entitled "Catalyst and Methods for Reforming Oxygenated Compounds"), all of which are incorporated herein by reference.

Similar to petroleum refining systems, biomass catalytic conversion processes require certain processing steps to maintain the effectiveness of the catalyst. Carbonaceous deposits build up on the catalyst surface through minor side reactions of the biomass and other generated products. As these deposits accumulate, access to the catalytic sites on the surface become restricted and the catalyst performance declines, resulting in lower conversion and yields. As a result, process steps are required to remove the deposits and return the catalyst to its desired level of functionality.

A need exists for systems that convert biomass to oxygenated compounds suitable for bioreforming processes, such as APR and HDO. Ideally, the system would convert in a continuous process most if not all of the biomass to compounds, such as starches, saccharides, sugars, sugar alcohols, and other oxygenated products, which are desirable feedstock for bioreforming processes. The system would also allow for operation in either a batch or continuous manner, and provide for the ability to regenerate catalyst without significant interruption to the conversion process.

SUMMARY

The invention provides methods for converting a biomass slurry comprising water and a biomass component to lower molecular weight oxygenated hydrocarbons. The method generally involves: (1) catalytically reacting the biomass slurry with hydrogen and a heterogeneous liquefaction catalyst at a liquefaction temperature and a liquefaction pressure to produce a product stream comprising the heterogeneous liquefaction catalyst, extractives and a solution comprising lower molecular weight oxygenated hydrocarbons; (2) separating the heterogeneous liquefaction catalyst and extractives from the product stream to provide a liquid stream comprising lower molecular weight oxygenated hydrocarbons; (3) washing the heterogeneous liquefaction catalyst in a washing medium; (4) regenerating the heterogeneous liquefaction catalyst in a regenerant gas at a regenerating pressure and regenerating temperature wherein carbonaceous deposits are removed from the heterogeneous liquefaction catalyst; and (5) reintroducing the heterogeneous liquefaction catalyst to the biomass slurry.

One aspect of the invention is the composition of the biomass component. In one embodiment, the biomass component comprises at least one member selected from the group including lignocellulose, lignin, hemicellulose, cellulose, recycled fiber, wood, wood residue, energy crops, agricultural waste, corn stover, bagasse, switch grass, miscanthus, and sorghum.

In one embodiment, the oxygenated hydrocarbon is selected from the group consisting of a starch, a carbohydrate, a polysaccharide, a disaccharide, a monosaccharide, a sugar, a sugar alcohol, an alditol, an organic acid, a phenol, a cresol, ethanediol, ethanedione, acetic acid, propanol, propanediol, propionic acid, glycerol, glyceraldehyde, dihydroxyacetone, lactic acid, pyruvic acid, malonic acid, a butanediol, butanoic acid, an aldotetrose, tartaric acid, an aldopentose, an aldohexose, a ketotetrose, a ketopentose, a ketohexose, a hemicellulose, a cellulosic derivative, a lignocellulosic derivative, a mono-oxygenated hydrocarbon, and a polyol.

The biomass slurry is converted in the presence of a heterogeneous liquefaction catalyst. In one embodiment, the heterogeneous liquefaction catalyst comprises an acidic resin or a basic resin. In another embodiment, the heterogeneous liquefaction catalyst comprises a support and a member adhered to the support, wherein the member is selected from the group consisting of Cu, Fe, Ru, Ir, Co, Rh, Pt, Pd, Ni, W, Mo, an alloy thereof, and combinations thereof. The heterogeneous liquefaction catalyst may further comprise a member selected from the group consisting of Cu, Mn, Cr, Mo, B, W, V, Nb, Ta, Ti, Zr, Y, La, Sc, Zn, Cd, Ag, Au, Sn, Ge, P, Al, Ga, In, Tl, an alloy thereof, and combinations thereof. The support may comprise a member selected from group consisting of a nitride, carbon, silica, alumina, zirconia, titania, vanadia, ceria, boron nitride, heteropolyacid, kieselguhr, hydroxyapatite, zinc oxide, chromia, zeolite, and mixtures thereof. The support may be modified by treating the support with tungsten.

The liquefaction is conducted at a temperature and pressure favorable to liquefaction. In one embodiment, the liquefaction temperature is in the range of about 80° C. to 350° C. and the liquefaction pressure is in the range of about 100 psi to 2000 psi.

Another aspect of the invention is washing the heterogeneous liquefaction catalyst in a washing medium. In one embodiment, the washing medium comprises a liquid selected from the group consisting of water, an acid, a base, a chelating agent, an alcohol, a ketone, a cyclic ether, a hydroxyketone, an aromatic, a paraffin, and combinations of the foregoing. In another embodiment, the step of washing the heterogeneous liquefaction catalyst comprises a first step of washing the heterogeneous liquefaction catalyst with a first washing solvent and a second step of washing the heterogeneous liquefaction catalyst with a second washing solvent. The first washing solvent may comprise a liquid selected from the group consisting of water, an acid, a base, a chelating agent, and combinations of the foregoing, and the second washing solvent may comprise a liquid selected from the group consisting of water, an alcohol, a ketone, a cyclic ether, a hydroxyketone, an aromatic, a paraffin, and combinations of the foregoing. Alternatively, the first washing solvent may comprise a liquid selected from the group consisting of water, an alcohol, a ketone, a cyclic ether, a hydroxyketone, an aromatic, a paraffin, and combinations of the foregoing, and the second washing solvent may comprise a liquid selected from the group consisting of water, an acid, a base, a chelating agent, and combinations of the foregoing.

The heterogeneous liquefaction catalyst regeneration is conducted at a temperature and pressure where regeneration conditions are favorable. In one embodiment, the regeneration temperature is in the range of about 300° C. to about 500° C. and is adjusted at a rate of about 20° C. per hour to about 60° C. per hour. In another embodiment, the regeneration pressure is between atmospheric pressure and about 500 psig. The regenerant gas may comprise oxygen or hydrogen. In one embodiment, the regeneration removes more than 90% of the carbonaceous deposits from the heterogeneous liquefaction catalyst.

In one aspect, the method further comprises the step of further processing the lower molecular weight oxygenated hydrocarbons to produce $C_{4+}$ compounds.

The invention also provides a method of converting a biomass slurry comprising water and a biomass component to lower molecular weight oxygenated hydrocarbons. The method includes the steps of: (1) catalytically reacting the biomass slurry with a biomass processing solvent comprising a $C_{2+}O_{1-3}$ hydrocarbon, hydrogen, and a heterogeneous liquefaction catalyst at a liquefaction temperature and a liquefaction pressure to produce a product stream comprising the heterogeneous liquefaction catalyst, extractives and a solution comprising lower molecular weight oxygenated hydrocarbons, wherein the biomass processing solvent is produced by catalytically reacting in the liquid or vapor phase an aqueous feedstock portion of the solution comprising water and a water-soluble oxygenated hydrocarbons comprising a $C_{2+}O_{1+}$ hydrocarbon with $H_2$ in the presence of a deoxygenation catalyst at a deoxygenation temperature and deoxygenation pressure; (2) separating the heterogeneous liquefaction catalyst and extractives from the product stream to provide a liquid stream comprising lower molecular weight oxygenated hydrocarbons; (3) washing the heterogeneous liquefaction catalyst in a washing medium; (4) regenerating the heterogeneous liquefaction catalyst in a regenerant gas at a regenerating pressure and regenerating temperature wherein carbonaceous deposits are removed from the heterogeneous liquefaction catalyst; and (5) reintroducing the heterogeneous liquefaction catalyst to the biomass slurry.

In one embodiment, the oxygenated hydrocarbon comprises a member selected from the group consisting of a lignocellulose derivative, a cellulose derivative, a hemicellulose derivative, a carbohydrate, a starch, a monosaccharide, a disaccharide, a polysaccharide, a sugar, a sugar alcohol, an alditol, and a polyol. The biomass hydrolysate may be recycled and combined with the biomass slurry.

One aspect of the invention is the biomass processing solvent, which may comprise a member selected from the group consisting of an alcohol, ketone, aldehyde, cyclic ether, ester, diol, triol, hydroxy carboxylic acid, carboxylic acid, and a mixture thereof. In one embodiment, the biomass processing solvent comprises a member selected from the group consisting of ethanol, n-propyl alcohol, isopropyl alcohol, butyl alcohol, pentanol, hexanol, cyclopentanol, cyclohexanol, 2-methylcyclopentanol, a hydroxyketone, a cyclic ketone, acetone, propanone, butanone, pentanone, hexanone, 2-methyl-cyclopentanone, ethylene glycol, 1,3-propanediol, propylene glycol, butanediol, pentanediol, hexanediol, methylglyoxal, butanedione, pentanedione, diketohexane, a hydroxyaldehyde, acetaldehyde, propionaldehyde, butyraldehyde, pentanal, hexanal, formic acid, acetic acid, propionic acid, butanoic acid, pentanoic acid, hexanoic acid, lactic acid, glycerol, furan, tetrahydrofuran, dihydrofuran, 2-furan methanol, 2-methyl-tetrahydrofuran, 2,5-dimethyl-tetrahydrofuran, 2-ethyl-tetrahydrofuran, 2-methyl furan, 2,5-dimethyl furan, 2-ethyl furan, hydroxylmethylfurfural, 3-hydroxytetrahydrofuran, tetrahydro-3-furanol, 5-hydroxymethyl-2 (5H)-furanone, dihydro-5-(hydroxymethyl)-2(3H)-furanone, tetrahydro-2-furoic acid, dihydro-5-(hydroxymethyl)-2(3H)-furanone, tetrahydrofurfuryl alcohol, 1-(2-furyl)ethanol, and hydroxymethyltetrahydrofurfural, isomers thereof, and combinations thereof.

The deoxygenation catalyst is capable of deoxygenating water-soluble oxygenated hydrocarbons to produce the biomass processing solvent. In one embodiment, the deoxygenation catalyst comprises a support and a member selected from the group consisting of Re, Cu, Fe, Ru, Ir, Co, Rh, Pt, Pd, Ni, W, Os, Mo, Ag, Au, an alloy thereof, and a combination thereof. The deoxygenation catalyst may further comprise a member selected from the group consisting of Mn, Cr, Mo, W, V, Nb, Ta, Ti, Zr, Y, La, Sc, Zn, Cd, Ag, Au, Sn, Ge, P, Al, Ga, In, Tl, and a combination thereof. The deoxygenation catalyst may have an active metal function and an acidic function. The support may comprise a member selected from group consisting of a carbon, silica, alumina, zirconia, titania, tungsten, vanadia, heteropolyacid, kieselguhr, hydroxyapatite, chromia, zeolites, and mixtures thereof. The support may be a member selected from the group consisting of tungstated zirconia, tungsten modified zirconia, tungsten modified alpha-alumina, or tungsten modified theta alumina.

The deoxygenation temperature may be greater than 120° C., or 150° C., or 180° C., or 200° C., and less than 325° C., or 300° C., or 280° C., or 260° C., or 240° C., or 220° C. The deoxygenation pressure may be greater than 200 psig, or 365 psig, or 500 psig, or 600 psig, and less than 2500 psig, or 2250 psig, or 2000 psig, or 1800 psig, or 1500 psig, or 1200 psig, or 1000 psig, or 725 psig. The deoxygenation temperature may also be in the range of about 120° C. to 325° C., and the deoxygenation pressure is at least 0.1 atmosphere. In other embodiments, the deoxygenation temperature is in the range of about 120° C. to about 325° C., or about 200° C. to 280° C., and the deoxygenation pressure is between about 365 psig and about 2500 psig, or between about 500 and 2000 psig, or between about 600 and 1800 psig, or between about 365 and 1500 psig.

DETAILED DESCRIPTION OF THE INVENTION

The present invention relates to methods, reactor systems, and catalysts for converting biomass in a continuous process to a less complex liquid feedstock of oxygenated hydrocarbons for use in downstream bioreforming processes to produce biofuels and chemicals. The invention includes methods of converting the soluble and insoluble components of biomass, such as hemicellulose, cellulose and lignin, to water-soluble materials, including lignocellulosic derivatives, cellulosic derivatives, hemicellulosic derivatives, carbohydrates, starches, polysaccharides, disaccharides, monosaccharides, sugars, sugar alcohols, alditols, polyols, diols, alcohols, ketones, cyclic ethers, esters, carboxylic acids, aldehydes, and mixtures thereof, using hydrogen and a heterogeneous liquefaction catalyst. In some instances, the materials may also include water-insoluble materials in an organic phase containing longer chain oxygenated compounds that will segregate from the aqueous phase.

As used herein, the term "biomass" refers to, without limitation, organic materials produced by plants (such as leaves, roots, seeds and stalks), and microbial and animal metabolic wastes. Common biomass sources include: (1) agricultural residues, including corn stover, straw, seed hulls, sugarcane leavings, bagasse, nutshells, cotton gin trash, and manure from cattle, poultry, and hogs; (2) wood materials, including wood or bark, sawdust, timber slash, and mill scrap; (3) municipal solid waste, including recycled paper, waste paper and yard clippings; and (4) energy crops, including poplars, willows, switch grass, miscanthus, sorghum, alfalfa, prairie bluestream, corn, soybean, and the like. The term also refers to the primary building blocks of the above, namely, lignin, cellulose, hemicellulose and carbohydrates, such as saccharides, sugars and starches, among others.

As used herein, the term "bioreforming" refers to, without limitation, processes for catalytically converting biomass and other carbohydrates to lower molecular weight hydrocarbons and oxygenated compounds, such as alcohols, ketones, cyclic ethers, esters, carboxylic acids, aldehydes, diols and other polyols, using aqueous phase reforming, hydrogenation, hydrogenolysis, hydrodeoxygenation and/or other conversion processes involving the use of heterogeneous catalysts. Bioreforming also includes the further catalytic conversion of such lower molecular weight oxygenated compounds to $C_{4+}$ compounds.

Figure 1:
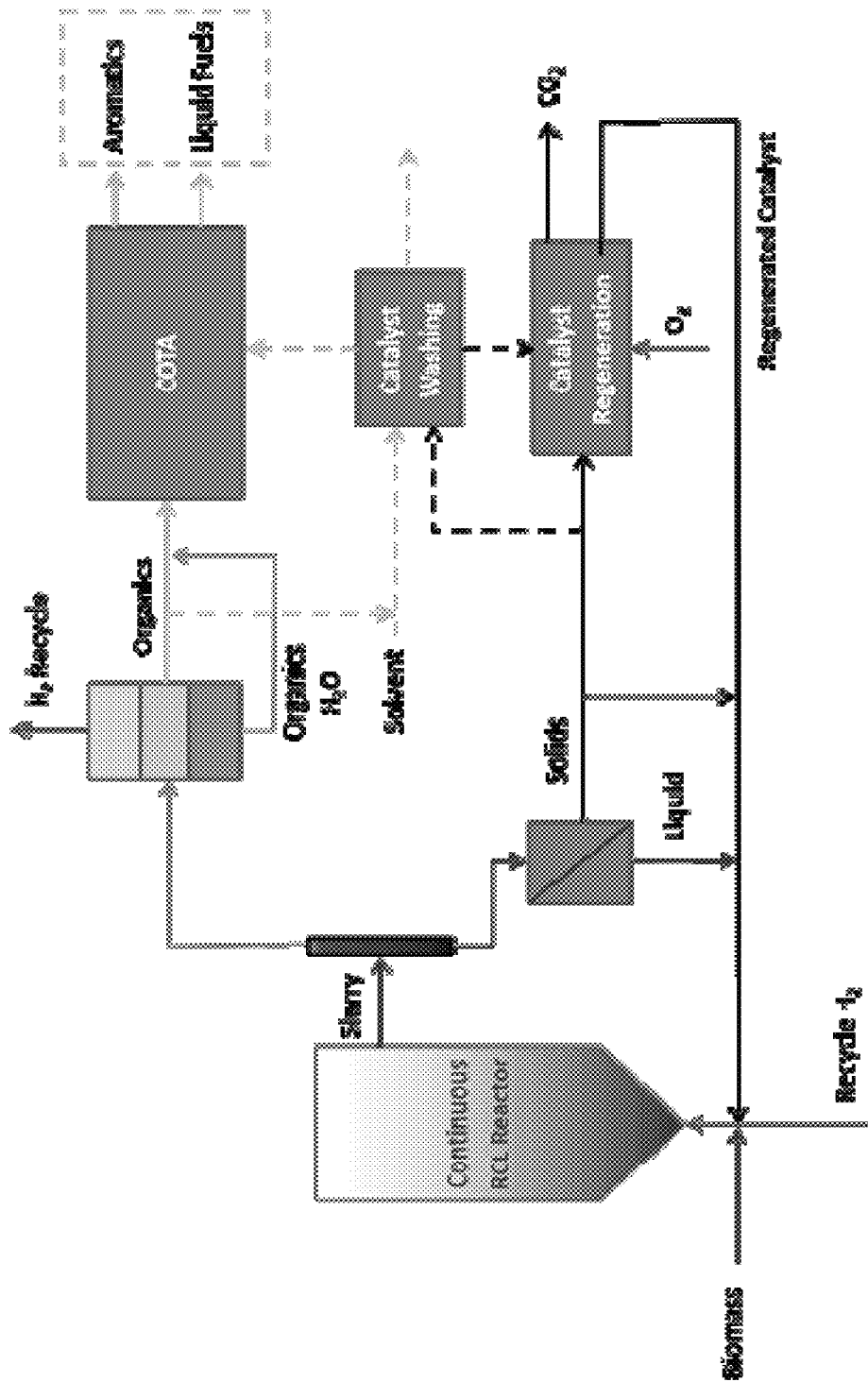
FIG. 1 is a flow diagram illustrating one embodiment of the present invention.

In the present invention, the soluble and insoluble portions of the biomass are converted to water-soluble oxygenated compounds using hydrogen and a heterogeneous liquefaction catalyst in a continuous process. The general process is illustrated in FIG. 1. A biomass slurry is created by combining biomass that has been chopped, shredded, pressed, ground or processed to a size amenable for conversion. The biomass slurry is then passed into a reactor where it reacts with hydrogen and a heterogeneous liquefaction catalyst at a liquefaction temperature and a liquefaction pressure to cause a reaction that converts all or at least a portion of the lignin, cellulose and hemicellulose to a biomass product stream that includes the heterogeneous liquefaction catalyst, a liquid solution of oxygenated compounds, extractives and unreacted or under-reacted biomass. In some instances, the solution may include both an aqueous phase and an organic phase containing longer chain oxygenated compounds that segregate from the aqueous phase.

Figure 2:
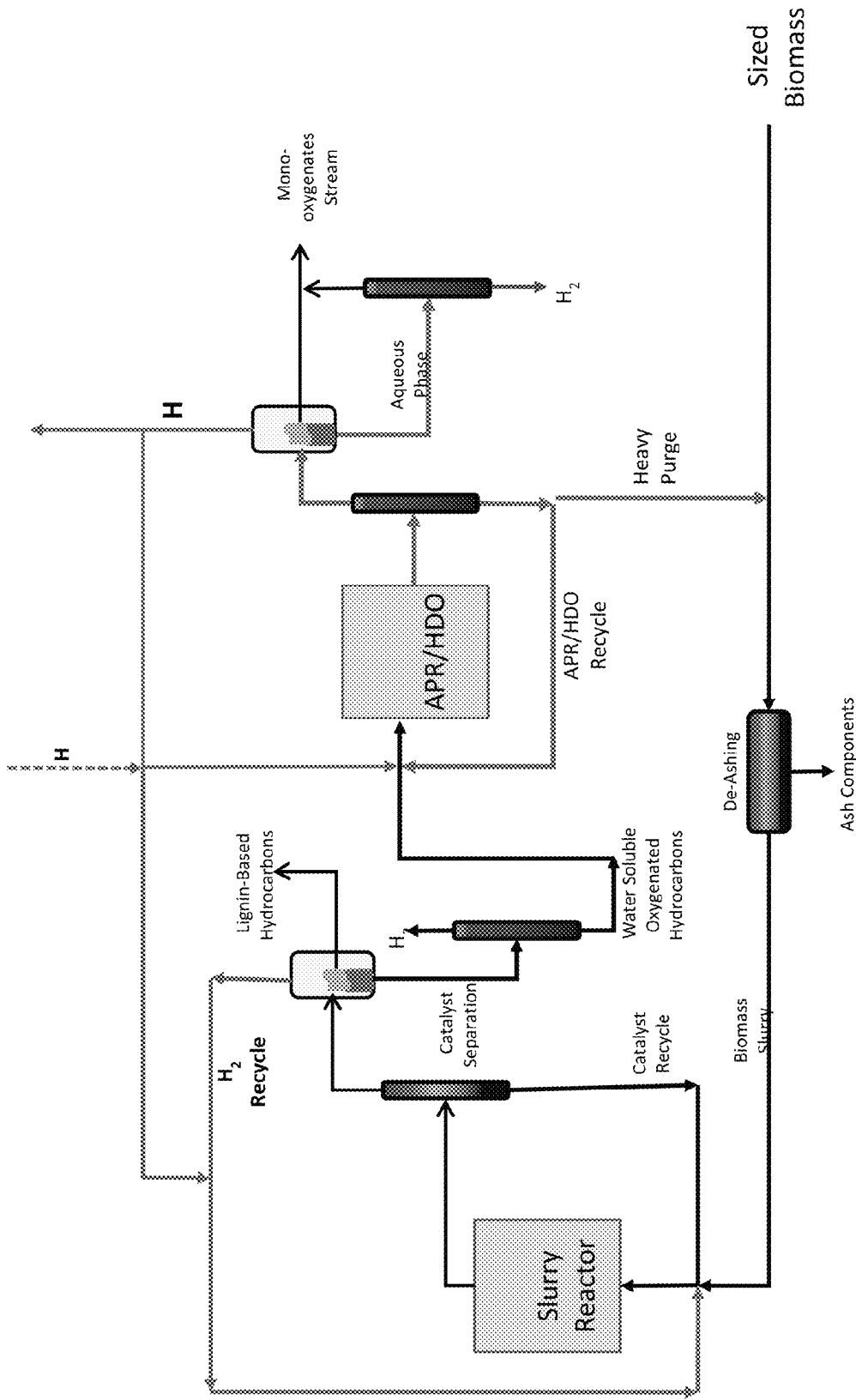
FIG. 2 is a flow diagram illustrating a process for catalytically converting biomass to liquid fuels using a biomass processing solvent derived from the conversion of biomass hydrolysate in an APR/HDO process.
Figure 3:
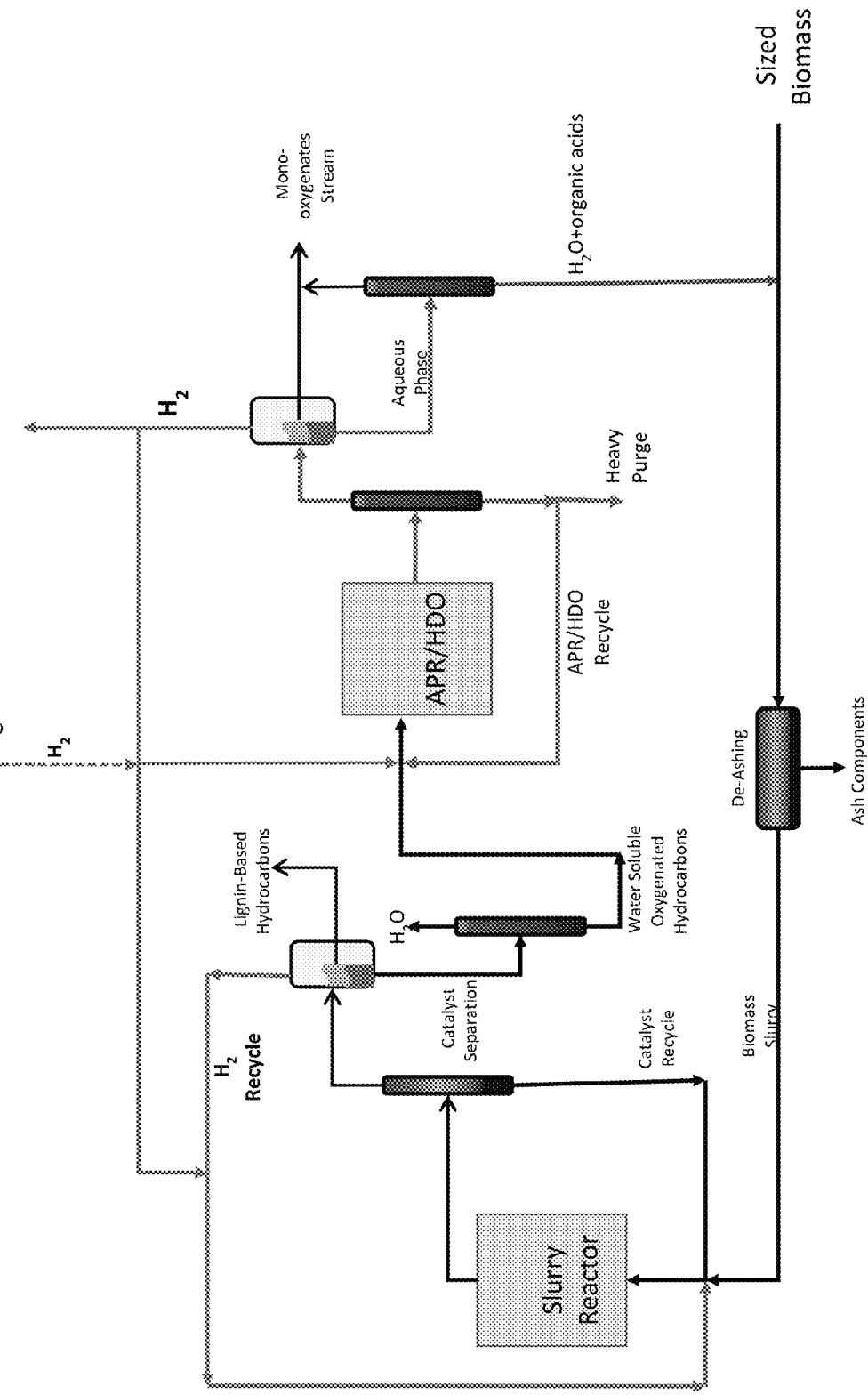
FIG. 3 is a flow diagram illustrating a process for catalytically converting biomass to liquid fuels using water and organic acids derived from the conversion of biomass hydrolysate in an APR/HDO process as a biomass processing solvent.

In a second embodiment, the present invention uses hydrogen, a heterogeneous liquefaction catalyst and a biomass processing solvent or solvent mixture produced in a bioreforming process, as illustrated in FIGS. 2 and 3. The biomass processing solvent or solvent mixture may contain a wide range of oxygenates, such as ketones, alcohols, cyclic ethers, acids, and esters, and/or $C_{4+}$ hydrocarbons, such as $C_{4+}$ alkanes, $C_{4+}$ alkenes, and aromatic compounds, including benzene, toluene, xylene. In a preferred embodiment, the biomass processing solvent or solvent mixture is derived from the biomass hydrolysate or, as illustrated in FIGS. 2 and 3, from the further processing of the biomass hydrolysate in a bioreforming process.

The composition of the biomass product stream will vary depending on the process conditions and the particular type of biomass feedstock employed. The liquid solution of oxygenated compounds will generally include an aqueous phase containing water, carbohydrates, starches, polysaccharides, disaccharides, monosaccharides, sugars, sugar alcohols, alditols, mono-oxygenates, organic acids, phenols, cresols and, in some instances, an organic phase containing longer chain oxygenated compounds. In one embodiment, the oxygenated compounds in the aqueous phase include, without limitation, sugar, sugar alcohols, starch, saccharides and other polyhydric alcohols. Preferably, the aqueous phase includes one or more sugars, such as glucose, fructose, sucrose, maltose, lactose, mannose or xylose, or sugar alcohols, such as arabitol, erythritol, glycerol, isomalt, lactitol, malitol, mannitol, sorbitol, xylitol, arabitol, or glycol. In other embodiments, the aqueous phase also includes alcohols, ketones, cyclic ethers, esters, carboxylic acids, aldehydes, diols and other polyols that may be useful as the solvent. The aqueous phase may also include mono-oxygenated hydrocarbons that may be further converted to $C_{4+}$ hydrocarbons, such as $C_{4+}$ alkanes, $C_{4+}$ alkenes, and aromatic compounds, including benzene, toluene, and xylene, which are useful as liquid fuels and chemicals. Extractives will typically include ash, terpenoids, stilbenes, flavonoids, proteins, and other inorganic products. The product stream may also include unreacted or under-reacted biomass, typically in a solid form.

Following conversion, the biomass product stream undergoes one or more separation steps to separate the heterogeneous liquefaction catalyst, extractives, unreacted biomass and under-reacted biomass from the liquid solution of oxygenated compounds. Various separation techniques known in the art may be used. Such techniques may include, without limitation, gravitational settling techniques, cyclone separation techniques, simulated moving bed technology, distillation, filtration, etc. In one embodiment, the biomass product stream is directed into a settling tank configured to allow a bottom portion containing solid materials (e.g., the heterogeneous liquefaction catalyst, extractives and unreacted or under-reacted materials) to separate from a top portion containing a significant portion of the liquid solution of oxygenated compounds and residual or resulting gases generated in the system. In certain embodiments, a portion of the solution of oxygenated compounds may also be maintained in the bottom portion to assist with the movement of the solid materials through additional processing steps or for recycle to the biomass slurry for use as a solvent.

The removal of the heterogeneous liquefaction catalyst, extractives, unreacted biomass and under-reacted biomass from the biomass product stream provides a bioreforming feedstock stream containing oxygenated compounds. In certain applications, the feedstock stream may also require further processing to separate aqueous phase products from organic phase products, such as lignin-based hydrocarbons not suitable for further conversion. The feedstock stream may also be dewatered or further purified prior to being introduced into further processing steps. Such dewatering and purification processes are known in the art and can include simulated moving bed technology, distillation, filtration, etc.

In one embodiment, the resulting oxygenated compounds are collected for further processing in a bioreforming process or, alternatively, used as a feedstock for other conversion processes, including the production of fuels and chemicals using fermentation or enzymatic technologies. For example, water-soluble carbohydrates, such as starch, monosaccharides, disaccharides, polysaccharides, sugars, and sugar alcohols, and water-soluble derivatives from the lignin, hemicellulose and cellulose are suitable for use in bioreforming processes, such as those described in U.S. Pat. Nos. 6,699, 457; 6,964,757; 6,964,758; and 7,618,612 (all to Cortright et al., and entitled "Low-Temperature Hydrogen Production from Oxygenated Hydrocarbons"); U.S. Pat. No. 6,953,873 (to Cortright et al., and entitled "Low-Temperature Hydrocarbon Production from Oxygenated Hydrocarbons"); U.S. Pat. Nos. 7,767,867 and 7,989,664 and U.S. Application Ser. No. 2011/0306804 (all to Cortright, and entitled "Methods and Systems for Generating Polyols"); U.S. Patent Application Ser. Nos. 2008/0216391; 2008/0300434; and 2008/0300435 (all to Cortright and Blommel, and entitled "Synthesis of Liquid Fuels and Chemicals from Oxygenated Hydrocarbons"); U.S. Patent Application Ser. No. 2009/0211942 (to Cortright, and entitled "Catalysts and Methods for Reforming Oxygenated Compounds"); U.S. Patent Application Ser. No. 2010/0076233 (to Cortright et al., and entitled "Synthesis of Liquid Fuels from Biomass"); International Patent Application No. PCT/US2008/056330 (to Cortright and Blommel, and entitled "Synthesis of Liquid Fuels and Chemicals from Oxygenated Hydrocarbons"); and commonly owned co-pending International Patent Application No. PCT/US2006/048030 (to Cortright et al., and entitled "Catalyst and Methods for Reforming Oxygenated Compounds"), all of which are incorporated herein by reference.

Alternatively, the resulting biomass hydrolysate may be recycled and combined in the biomass slurry for further conversion.

Biomass Liquefaction

To produce the desired products, the biomass slurry is reacted with hydrogen over a heterogeneous liquefaction catalyst under conditions of temperature and pressure effective to convert the lignin, cellulose, hemicellulose and their derivatives, whether recycled or reactively generated in the slurry, to a liquid product stream containing one or more polysaccharides, disaccharides, monosaccharides, sugars, sugar alcohols, alditols, mono-oxygenates, organic acids, phenols, cresols and, in some instances, an organic phase containing longer chain oxygenated compounds. The specific oxygenated products produced will depend on various factors including the composition of the slurry (including the solvent, if any), reaction temperature, reaction pressure, water concentration, hydrogen concentration, reaction byproducts, the reactivity of the heterogeneous liquefaction catalyst, and the flow rate of the slurry as it affects the space velocity (the mass/volume of reactant per unit of catalyst per unit of time), gas hourly space velocity (GHSV), and weight hourly space velocity.

The liquefaction process can be either batch or continuous. In one embodiment, the liquefaction process is a continuous process using one or more continuous stirred-tank reactors in parallel or in series. In another embodiment, the liquefaction step is conducted in a single reactor with the below described deoxygenation step.

The liquefaction catalyst is a heterogeneous catalyst having one or more materials capable of catalyzing a reaction between hydrogen and lignin, cellulose, hemicellulose and their derivatives, to produce the desired oxygenated compounds. The heterogeneous liquefaction catalyst may include, without limitation, an acid modified resin, a base modified resin, and/or one or more of Cu, Fe, Ru, Ir, Co, Rh, Pt, Pd, Ni, W, Mo, Zr, alloys and combinations thereof. The catalyst may also include these elements alone or combined with one or more Cu, Mn, Cr, Mo, B, W, V, Nb, Ta, Ti, Zr, Y, La, Sc, Zn, Cd, Ag, Au, Sn, Ge, P, Al, Ga, In, Tl, Ce, alloys, and combinations thereof. In one embodiment, the catalyst includes Ni, Ru, Ir, Pt, Pd, Rh, Co, or Mo and at least one member selected from W, B, Pt, Sn, Ag, Au, Rh, Co, and Mo.

Resins will generally include basic or acidic supports (e.g., supports having low isoelectric points) which are able to catalyze liquefaction reactions of biomass, followed by hydrogenation reactions in the presence of $H_2$, leading to carbon atoms that are not bonded to oxygen atoms. One such class of acidic supports are heteropolyacids, solid-phase acids exemplified by such species as $H_{3+x}PMo_{12-x}V_xO_{40}$, $H_4SiW_{12}O_{40}$, $H_3PW_{12}O_{40}$, and $H_6P_2W_{18}O_{62}$. Heteropolyacids also have a well-defined local structure, the most common of which is the tungsten-based Keggin structure. Basic resins include resins that exhibit basic functionality, such as Amberlyst.

The liquefaction catalyst is either self-supporting or includes a supporting material. The support may contain any one or more of nitride, carbon, silica, alumina, zirconia, titania, tungsten, vanadia, ceria, zinc oxide, chromia, boron nitride, tungstated zirconia, heteropolyacids, kieselguhr, hydroxyapatite, and mixtures thereof. Preferable supports are carbon, m-$ZrO_2$, and W—$ZrO_2$. In one embodiment, the deconstruction catalyst includes Ni:Mo, Pd:Mo, Rh:Mo, Co:Mo, Pd:Ru, Pt:Re, or Pt:Rh on a m-$ZrO_2$ support. In another embodiment, the deconstruction catalyst includes Ru, Ru:Pt, Pd:Ru, Pt:Re, Pt:Rh, Pd:Mo, Pd:Ag, or Ru:Pt:Sn on a carbon or W—$ZrO_2$ support. In yet another embodiment the catalyst includes Fe, Co, Ni, Cu, Ru, Rh, Pd, Pt, Re, Mo, or W, on a carbon support. The support may also serve as a functional catalyst, such as in the case of acidic or basic resins or supports having acidic or basic functionality.

In one embodiment, the catalyst is formed in a honeycombed monolith design such that the biomass slurry, solid phase slurry or the solid/liquid phase slurry can flow through the monolithic channels. In another embodiment, the catalyst includes a magnetic element such as Fe or Co such that the catalyst can be easily separated from the resulting biomass product stream.

The liquefaction temperature will generally be greater than 80° C., or 120° C., or 150° C., or 180° C., or 250° C., and less than 350° C., or 325° C., or 300° C., or 260° C. The liquefaction pressure will generally be greater than 100 psi, or 250 psi, or 300 psi, or 625 psi, or 900 psi, or 1000 psi, or 1200 psi, and less than 2000 psi, or 1500 psi, or 1200 psi. In one embodiment, the liquefaction pressure is between about 100 psi and 2000 psi, or between about 300 psi and 1500 psi, or between about 1000 psi and 1500 psi. In another embodiment, the liquefaction temperature is between about 80° C. and 350° C., or between about 150° C. and 350° C., or between about 150° C. and 300° C., or between about 200° C. and 260° C., or between about 250° C. and 300° C.

The reaction should be conducted under conditions where the residence time of the slurry over the heterogeneous liquefaction catalyst is appropriate to generate the desired products in a liquid phase. For example, the WHSV for the reaction may be at least about 0.1 gram of biomass per gram of catalyst per hour, and more preferably the WHSV is about 0.1 to 40.0 g/g hr., including a WHSV of about 0.25, 0.5, 0.75, 1.0, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6, 7, 8, 9, 10, 11, 12, 13, 14, 15, 20, 25, 30, 35, 40 g/g hr., and ratios between (including 0.83, 0.85, 1.71, 1.72, 1.73, etc.). Preferably, the biomass slurry contacts the catalyst for between approximately 5 minutes and 2 hours.

The present invention is able to effectively convert the biomass components to lower molecular weight oxygenated hydrocarbons due to the presence of hydrogen in the system. The hydrogen facilitates the reaction and conversion process by immediately reacting with the various reaction intermediates and the catalyst to produce products that are more stable and less subject to degradation. The hydrogen may be generated in situ using aqueous phase reforming (in situ-generated $H_2$ or APR $H_2$), whether in the biomass liquefaction reactor or in downstream processes using the biomass hydrolysate as a feedstock, or a combination of APR $H_2$, external $H_2$ or recycled $H_2$, or just simply external $H_2$ or recycled $H_2$. The term "external $H_2$" refers to hydrogen that does not originate from the biomass solution, but is added to the reactor system from an external source. The term "recycled $H_2$" refers to unconsumed hydrogen which is collected and then recycled back into the reactor system for further use. External $H_2$ and recycled $H_2$ may also be referred to collectively or individually as "supplemental $H_2$." In general, the amount of $H_2$ added should maintain the reaction pressure within the system at the desired levels, or increase the molar ratio of hydrogen to carbon and/or oxygen in order to enhance the production yield of certain reaction product types.

The liquefaction process may also include the introduction of supplemental materials to the slurry to assist with the liquefaction or the further conversion of the oxygenated compounds to products more suited for bioreforming processes.

Supplemental materials may include solvents that aid in the liquefaction process, such as acetone, gluconic acid, acetic acid, $H_2SO_4$ and $H_3PO_4$ and solvents derived from a bioreforming process, such as those described in U.S. Pat. Nos. 7,767,867 and 7,989,664 and U.S. Application Ser. No. 2011/0306804 (all to Cortright, and entitled "Methods and Systems for Generating Polyols"). Supplemental materials may also include unreacted or under-reacted materials recycled from the product stream.

Solvent-based applications are well known in the art. Organosolv processes use organic solvents such as ionic liquids, acetone, ethanol, 4-methyl-2-pentanone, and solvent mixtures, to fractionate lignocellulosic biomass into cellulose, hemicellulose, and lignin streams (Paszner 1984; Muurinen 2000; and Bozell 1998). Strong-acid processes use concentrated hydrochloric acid, phosphoric acid, sulfuric acid or other strong organic acids as the depolymerization agent, while weak acid processes involve the use of dilute strong acids, acetic acid, oxalic acid, hydrofluoric acid, or other weak acids as the solvent. Enzymatic processes have also recently gained prominence and include the use of enzymes as a biocatalyst to decrystalize the structure of the biomass and allow further hydrolysis to useable feedstocks.

Production of a Biomass Processing Solvent

Bioreforming processes convert starches, sugars and other polyols to a wide range of oxygenates, including organic compounds that facilitate biomass liquefaction. As shown in Table 1 below, the bioreforming process produces a complex mixture of oxygenates. The mixture of different oxygenates provides good candidate compounds for a high quality solvent.

TABLE 1

Typical Products of a Bioreforming Process

| Aqueous Phase | | Organic Phase | |
| --- | --- | --- | --- |
| Component | % of Phase | Component | % of Phase |
| 2-Pentanone | 13.75 | 3-Hexanone | 12.98 |
| Butanoic acid | 13.61 | 2-Hexanone | 12.60 |
| 2-Butanone | 13.08 | 2-Pentanone | 9.53 |
| Furan, tetrahydro-2,5-dimethyl- | 10.70 | Water | 6.64 |
| | | Butanoic acid | 6.19 |
| Acetone | 8.43 | 2-Furanmethanol, tetrahydro- | 5.68 |
| Propionic Acid | 8.15 | Furan, tetrahydro-2,5-dimethyl- | 5.29 |
| Acetic acid | 4.82 | 3-Pentanone | 4.93 |
| Pentanoic acid | 4.68 | Pentanoic acid | 4.41 |
| 2-Butanol, (+/−)- | 3.77 | 2-Butanone | 4.35 |
| 2-Hexanone | 3.75 | 2H-Pyran, tetrahydro-2-methyl- | 2.78 |
| 3-Hexanone | 3.57 | 2-Hexanol | 2.22 |
| (R)-(−)-2-Pentanol | 1.82 | Hexanoic acid | 2.10 |
| Isopropyl Alcohol | 1.73 | Furan, tetrahydro-2-methyl- | 1.95 |
| Hexanoic acid | 1.09 | 2(3H)-Furanone, 5- | 1.71 |
| 2-Butanone, 3-hydroxy- | 1.05 | ethyldihydro- | |
| | | 2-Pentanol | 1.71 |
| | | 3-Hexanol | 1.62 |
| | | Hexane | 1.55 |
| | | Pentane | 1.52 |
| | | Propionic Acid | 1.42 |

As used herein, "oxygenates" generically refers to hydrocarbon compounds having 2 or more carbon atoms, and 1 to 3 oxygen atoms (referred to herein as $C_{2+}O_{1-3}$ hydrocarbons), such as alcohols, ketones, aldehydes, cyclic ethers, esters, hydroxy carboxylic acids, carboxylic acids, diols and triols. Preferably, oxygenates have from 2 to 6 carbon atoms, or 3 to 6 carbon atoms, and 1, 2 or 3 oxygen atoms. Alcohols may include, without limitation, cyclic alcohols or primary, secondary, linear, branched $C_{2+}$ alcohols, such as ethanol, n-propyl alcohol, isopropyl alcohol, butyl alcohol, isobutyl alcohol, butanol, pentanol, cyclopentanol, hexanol, cyclohexanol, 2-methyl-cyclopentanonol, heptanol, octanol, nonanol, decanol, undecanol, dodecanol, and isomers thereof. The ketones may include, without limitation, hydroxyketones, cyclic ketones, diketones, acetone, propanone, 2-oxopropanal, butanone, butane-2,3-dione, 3-hydroxybutan-2-one, pentanone, cyclopentanone, pentane-2,3-dione, pentane-2,4-dione, cyclohexanone, 2-methyl-cyclopentanone, hexanone, heptanone, octanone, nonanone, decanone, undecanone, dodecanone, methylglyoxal, butanedione, pentanedione, diketohexane, and isomers thereof. The aldehydes may include, without limitation, hydroxyaldehydes, acetaldehyde, propionaldehyde, butyraldehyde, pentanal, hexanal, heptanal, octanal, nonal, decanal, undecanal, dodecanal, and isomers thereof. The carboxylic acids may include, without limitation, formic acid, acetic acid, propionic acid, butanoic acid, pentanoic acid, hexanoic acid, heptanoic acid, isomers and derivatives thereof, including hydroxylated derivatives, such as 2-hydroxybutanoic acid and lactic acid. The diols may include, without limitation, lactones, ethylene glycol, propylene glycol, 1,3-propanediol, butanediol, pentanediol, hexanediol, heptanediol, octanediol, nonanediol, decanediol, undecanediol, dodecanediol, and isomers thereof. The triols may include, without limitation, glycerol, 1,1,1 tris(hydroxymethyl)-ethane (trimethylolethane), trimethylolpropane, hexanetriol, and isomers thereof. Cyclic ethers include, without limitation, fufural, furan, tetrahydrofuran, dihydrofuran, 2-furan methanol, 2-methyl-tetrahydrofuran, 2,5-dimethyl-tetrahydrofuran, 2-methyl furan, 2-ethyl-tetrahydrofuran, 2-ethyl furan, hydroxylmethylfurfural, 3-hydroxytetrahydrofuran, tetrahydro-3-furanol, 2,5-dimethyl furan, 5-hydroxymethyl-2(5H)-furanone, dihydro-5-(hydroxymethyl)-2(3H)-furanone, tetrahydro-2-furoic acid, dihydro-5-(hydroxymethyl)-2(3H)-furanone, tetrahydrofurfuryl alcohol, 1-(2-furyl)ethanol, hydroxymethyltetrahydrofurfural, and isomers thereof.

The above oxygenates may originate from any source, but are preferably derived from oxygenated hydrocarbons resulting from the initial processing of the biomass in the biomass slurry. Preferably, the oxygenated hydrocarbon is any one or more water-soluble oxygenated hydrocarbons having two or more carbon atoms and at least one oxygen atom (referred to herein as $C_{2+}O_{1+}$ hydrocarbons). In one embodiment, the oxygenated hydrocarbon has 2-12 carbon atoms ($C_{2-12}O_{1-11}$ hydrocarbon), or 2-6 carbon atoms ($C_{2-6}O_{1-6}$ hydrocarbon), and 1, 2, 3, 4, 5 or 6 oxygen atoms. The oxygenated hydrocarbon may also have an oxygen-to-carbon ratio ranging from 0.5:1 to 1.5:1, including ratios of 0.75:1.0, 1.0:1.0, 1.25:1.0, 1.5:1.0, and other ratios between. In one example, the oxygenated hydrocarbon has an oxygen-to-carbon ratio of 1:1. Nonlimiting examples of preferred water-soluble oxygenated hydrocarbons include starches, monosaccharides, disaccharides, polysaccharides, sugar, sugar alcohols, alditols, ethanediol, ethanedione, acetic acid, propanol, propanediol, propionic acid, glycerol, glyceraldehyde, dihydroxyacetone, lactic acid, pyruvic acid, malonic acid, butanediols, butanoic acid, aldotetroses, tartaric acid, aldopentoses, aldohexoses, ketotetroses, ketopentoses, ketohexoses, alditols, hemicelluloses, cellulosic derivatives, lignocellulosic derivatives, starches, polyols and the like.

In applications employing a solvent, the solvent may be produced directly from a portion of the aqueous phase of the biomass product stream, or derived from alternative processes utilizing a separate feedstock stream containing water-soluble oxygenated hydrocarbons. The solvent is prepared by reacting an aqueous solution containing water-soluble oxygenated hydrocarbons with hydrogen over a deoxygenation catalyst to produce oxygenates that form the solvent. The hydrogen may be generated in situ using aqueous phase reforming, or a combination of APR $H_2$, external $H_2$ or recycled $H_2$, or just simply external $H_2$ or recycled $H_2$.

In processes utilizing APR $H_2$, the oxygenates are prepared by catalytically reacting a portion of the aqueous solution of oxygenated hydrocarbons in the presence of an APR catalyst at a reforming temperature and reforming pressure to produce the APR $H_2$, and catalytically reacting the APR $H_2$ (and recycled $H_2$ and/or external $H_2$) with a portion of the aqueous solution of oxygenated hydrocarbons in the presence of a deoxygenation catalyst at a deoxygenation temperature and deoxygenation pressure to produce the desired oxygenates. In systems utilizing recycled $H_2$ or external $H_2$ as a hydrogen source, oxygenates are simply prepared by catalytically reacting the recycled $H_2$ and/or external $H_2$ with the feedstock solution in the presence of the deoxygenation catalyst at the deoxygenation temperatures and pressures. In each of the above, oxygenates may also include recycled oxygenates (recycled $C_{2+}O_{1-3}$ hydrocarbons).

The deoxygenation catalyst is preferably a heterogeneous catalyst having one or more active materials capable of catalyzing a reaction between hydrogen and the oxygenated hydrocarbon to remove one or more of the oxygen atoms from the oxygenated hydrocarbon to produce alcohols, ketones, aldehydes, cyclic ethers, esters carboxylic acids, hydroxy carboxylic acids, diols or triols. In general, the heterogeneous deoxygenation catalyst will have both an active metal function and an acidic function to achieve the foregoing. Without being held to a specific theory, it is believed that the acidic function first catalyzes dehydration reactions of the oxygenated hydrocarbon. Hydrogenation reactions then occur on the metallic catalyst in the presence of $H_2$, producing carbon atoms not bonded to oxygen atoms. The bi-functional dehydration/hydrogenation pathway consumes $H_2$ and leads to the subsequent formation of the various polyols, diols, ketones, aldehydes, alcohols, carboxylic acids, hydroxy carboxylic acids, esters, and cyclic ethers, such as furans and pyrans.

The acidic and/or metallic functions are provided by active catalytic materials that include, without limitation, Cu, Re, Fe, Ru, Ir, Co, Rh, Pt, Pd, Ni, W, Os, Mo, Ag, Au, alloys thereof, and combinations thereof, adhered to a support. The deoxygenation catalyst may include these elements alone or in combination with one or more Mn, Cr, Mo, W, V, Nb, Ta, Ti, Zr, Y, La, Sc, Zn, Cd, Ag, Au, Sn, Ge, P, Al, Ga, In, Tl, Ce, and combinations thereof. In one embodiment, the deoxygenation catalyst includes Pt, Pd, Ru, Re, Ni, W or Mo. In yet another embodiment, the deoxygenation catalyst includes Sn, W, Mo, Ag, Fe and/or Re and at least one transition metal selected from Ni, Pd, Pt and Ru. In another embodiment, the catalyst includes Fe, Re and at least Cu or one Group VIIIB transition metal. In yet another embodiment, the deoxygenation catalyst includes Pd alloyed or admixed with Cu or Ag and supported on an acidic support. In yet another embodiment, the deoxygenation catalyst includes Pd alloyed or admixed with a Group VIB metal supported on an acidic support. In yet another embodiment, the deoxygenation catalyst includes Pd alloyed or admixed with a Group VIB metal and a Group IVA metal on an acidic support. The support may be any one of a number of supports, including a support having carbon, silica, alumina, zirconia, titania, tungsten, vanadia, chromia, zeolites, heteropolyacids, kieselguhr, hydroxyapatite, and mixtures thereof.

The deoxygenation catalyst may also be an acidic support modified or constructed to provide the desired functionality. Heteropolyacids are a class of solid-phase acids exemplified by such species as $H_{3+x}PMo_{12-x}V_xO_{40}$, $H_4SiW_{12}O_{40}$, $H_3PW_{12}O_{40}$, and $H_6P2W_{18}O_{62}$. Heteropolyacids are solid-phase acids having a well-defined local structure, the most common of which is the tungsten-based Keggin structure. Other examples may include, without limitation, tungstated zirconia, tungsten modified zirconia, tungsten modified alpha-alumina, or tungsten modified theta alumina.

Loading of the first element (i.e., Cu, Re, Fe, Ru, Ir, Co, Rh, Pt, Pd, Ni, W, Os, Mo, Ag, Au, alloys and combinations thereof) is in the range of 0.25 wt % to 25 wt %, with weight percentages of 0.10% and 0.05% increments between, such as 1.00%, 1.10%, 1.15%, 2.00%, 2.50%, 5.00%, 10.00%, 12.50%, 15.00% and 20.00%. The preferred atomic ratio of the second element (i.e., Mn, Cr, Mo, W, V, Nb, Ta, Ti, Zr, Y, La, Sc, Zn, Cd, Ag, Au, Sn, Ge, P, Al, Ga, In, Tl, Ce, and combinations thereof) is in the range of 0.25-to-1 to 10-to-1, including any ratios between, such as 0.50, 1.00, 2.50, 5.00, and 7.50-to-1. If the active catalytic materials are adhered to a support, the combination of the catalytic material and the support is from 0.25 wt % to 10 wt % of the primary element.

The water-to-carbon ratio on a molar basis for the aqueous solution of oxygenated hydrocarbons is preferably from about 0.5:1 to about 100:1, including ratios such as 1:1, 2:1, 3:1, 4:1, 5:1, 6:1, 7:1, 8:1, 9:1, 10:1, 15:1, 25:1, 50:1 75:1, 100:1, and any ratios there-between. The feedstock solution may also be characterized as a solution having at least 1.0 weight percent (wt %) of the total solution as an oxygenated hydrocarbon. For instance, the solution may include one or more oxygenated hydrocarbons, with the total concentration of the oxygenated hydrocarbons in the solution being at least about 1%, 5%, 10%, 20%, 30%, 40%, 50%, 60%, 70%, 80% or greater by weight, including any percentages between, and depending on the oxygenated hydrocarbons used. Water-to-carbon ratios and percentages outside of the above stated ranges are also included. Preferably the balance of the feedstock solution is water. In some embodiments, the feedstock solution consists essentially of water, one or more oxygenated hydrocarbons and, optionally, one or more feedstock modifiers described herein, such as alkali or hydroxides of alkali or alkali earth salts or acids. The feedstock solution may also include recycled oxygenated hydrocarbons recycled from the reactor system. The feedstock solution may also contain negligible amounts of hydrogen.

The feedstock solution is reacted with hydrogen in the presence of the deoxygenation catalyst at deoxygenation temperature and pressure conditions, and weight hourly space velocity, effective to produce the desired oxygenates. The specific oxygenates produced will depend on various factors, including the feedstock solution, reaction temperature, reaction pressure, water concentration, hydrogen concentration, the reactivity of the catalyst, and the flow rate of the feedstock solution as it affects the space velocity (the mass/volume of reactant per unit of catalyst per unit of time), gas hourly space velocity (GHSV), and weight hourly space velocity (WHSV). For example, an increase in flow rate, and thereby a reduction of feedstock exposure to the catalysts over time, will limit the extent of the reactions which may occur, causing increased yield for higher level diols and triols, with a reduction in ketone and alcohol yields.

The deoxygenation temperature and pressure are preferably selected to maintain at least a portion of the feedstock in the liquid phase at the reactor inlet. It is recognized, however, that temperature and pressure conditions may also be selected to more favorably produce the desired products in the vapor-phase or in a mixed phase having both a liquid and vapor phase. In general, the reaction should be conducted at process conditions wherein the thermodynamics of the proposed reaction are favorable. For instance, the minimum pressure required to maintain a portion of the feedstock in the liquid phase will likely vary with the reaction temperature. As temperatures increase, higher pressures will generally be required to maintain the feedstock in the liquid phase, if desired. Pressures above that required to maintain the feedstock in the liquid phase (i.e., vapor-phase) are also suitable operating conditions.

In general, the deoxygenation temperature should be greater than 120° C., or 150° C., or 180° C., or 200° C., and less than 325° C., or 300° C., or 280° C., or 260° C., or 240° C., or 220° C. The reaction pressure should be greater than 200 psig, or 365 psig, or 500 psig or 600 psig, and less than 2500 psig, or 2250 psig, or 2000 psig, or 1800 psig, or 1500 psig, or 1200 psig, or 1000 psig, or 725 psig. In one embodiment, the deoxygenation temperature is between about 150° C. and 300° C., or between about 200° C. and 280° C., or between about 220° C. and 260° C., or between about 150° C. and 260° C. In another embodiment, the deoxygenation pressure is between about 365 and 2500 psig, or between about 500 and 2000 psig, or between about 600 and 1800 psig, or between about 365 and 1500 psig.

A condensed liquid phase method may also be performed using a modifier that increases the activity and/or stability of the catalyst system. It is preferred that the water and the oxygenated hydrocarbon are reacted at a suitable pH of from about 1.0 to about 10.0, including pH values in increments of 0.1 and 0.05 between, and more preferably at a pH of from about 4.0 to about 10.0. Generally, the modifier is added to the feedstock solution in an amount ranging from about 0.1% to about 10% by weight as compared to the total weight of the deoxygenation catalyst system used, although amounts outside this range are included within the present invention.

In one embodiment, the deoxygenation step is performed in the same reactor as the liquefaction step. In this embodiment, the liquefaction temperature and deoxygenation temperature may be in the range of about 100° C. to 325° C., about 120° C. to 300° C., or about 200° C. to 280° C., and the liquefaction pressure and deoxygenation pressure may be in the range of about 200 psig to 1500 psig, about 200 psig to 1200 psig, or about 600 psig to 1800 psig.

In general, the reaction should be conducted under conditions where the residence time of the feedstock solution over the deoxygenation catalyst is appropriate to generate the desired oxygenates. For example, the WHSV for the reaction may be at least about 0.1 gram of oxygenated hydrocarbon per gram of catalyst per hour, and more preferably the WHSV is about 0.1 to 40.0 g/g hr., including a WHSV of about 0.25, 0.5, 0.75, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6, 7, 8, 9, 10, 11, 12, 13, 14, 15, 20, 25, 30, 35, 40 g/g hr., and ratios between (including 0.83, 0.85, 0.85, 1.71, 1.72, 1.73, etc.).

The hydrogen used in the deoxygenation reaction may be in-situ-generated $H_2$, external $H_2$ or recycled $H_2$. The amount (moles) of external $H_2$ or recycled $H_2$ introduced to the feedstock is between 0-100%, 0-95%, 0-90%, 0-85%, 0-80%, 0-75%, 0-70%, 0-65%, 0-60%, 0-55%, 0-50%, 0-45%, 0-40%, 0-35%, 0-30%, 0-25%, 0-20%, 0-15%, 0-10%, 0-5%, 0-2%, or 0-1% of the total number of moles of the oxygenated hydrocarbon(s) in the feedstock, including all intervals between. When the feedstock solution, or any portion thereof, is reacted with APR hydrogen and external $H_2$ or recycled $H_2$, the molar ratio of APR hydrogen to external $H_2$ (or recycled $H_2$) is at least 1:100, 1:50, 1:20; 1:15, 1:10, 1:5; 1:3, 1:2, 1:1, 2:1, 3:1, 5:1, 10:1, 15:1, 20:1, 50:1, 100:1 and ratios between (including 4:1, 6:1, 7:1, 8:1, 9:1, 11:1, 12:1, 13:1, 14:1, 15:1, 16:1, 17:1, 18:1 and 19:1, and vice-versa).

In-Situ Hydrogen Production

One advantage of the present invention is that it allows for the production and use of in-situ-generated $H_2$. The APR $H_2$ is produced from the feedstock under aqueous phase reforming conditions using an aqueous phase reforming catalyst (APR catalyst). The APR catalyst is preferably a heterogeneous catalyst capable of catalyzing the reaction of water and oxygenated hydrocarbons to form $H_2$ under the conditions described below. In one embodiment, the APR catalyst includes a support and at least one Group VIIIB metal, Fe, Ru, Ir, Co, Rh, Pt, Pd, Ni, alloys and combinations thereof. The APR catalyst may also include at least one additional material from Group VIIIB, Group VIIB, Group VIB, Group VB, Group IVB, Group IIB, Group IB, Group IVA or Group VA metals, such as Cu, B, Mn, Re, Cr, Mo, Bi, W, V, Nb, Ta, Ti, Zr, Y, La, Sc, Zn, Cd, Ag, Au, Sn, Ge, P, Al, Ga, In, Tl, Ce alloys and combinations thereof. The preferred Group VIIB metal includes Re, Mn, or combinations thereof. The preferred Group VIB metal includes Cr, Mo, W, or a combination thereof. The preferred Group VIIIB metals include Pt, Rh, Ru, Pd, Ni, or combinations thereof. The supports may include any one of the APR catalyst supports described below, depending on the desired activity of the APR catalyst system.

The APR catalyst may also be atomically identical to the deoxygenation catalyst, or combined with the deoxygenation catalyst to form a single catalyst system. For instance, the APR and deoxygenation catalyst may include Pt alloyed or admixed with Ni, Ru, Cu, Fe, Rh, Re, alloys and combinations thereof. The APR catalyst and deoxygenation catalyst may also include Ru alloyed or admixed with Ge, Bi, B, Ni, Sn, Cu, Fe, Rh, Pt, alloys and combinations thereof. The catalyst may also include Ni alloyed or admixed with Sn, Ge, Bi, B, Cu, Re, Ru, Fe, alloys and combinations thereof.

Preferred loading of the primary Group VIIIB metal is in the range of 0.25 wt % to 25 wt %, with weight percentages of 0.10% and 0.05% increments between, such as 1.00%, 1.10%, 1.15%, 2.00%, 2.50%, 5.00%, 10.00%, 12.50%, 15.00% and 20.00%. The preferred atomic ratio of the second material is in the range of 0.25-to-1 to 10-to-1, including ratios between, such as 0.50, 1.00, 2.50, 5.00, and 7.50-to-1.

A preferred APR catalyst composition is further achieved by the addition of oxides of Group IIIB, and associated rare earth oxides. In such event, the preferred components would be oxides of either lanthanum or cerium. The preferred atomic ratio of the Group IIIB compounds to the primary Group VIIIB metal is in the range of 0.25-to-1 to 10-to-1, including ratios between, such as 0.50, 1.00, 2.50, 5.00, and 7.50-to-1.

Another preferred APR catalyst composition is one containing platinum and rhenium. The preferred atomic ratio of Pt to Re is in the range of 0.25-to-1 to 10-to-1, including ratios there-between, such as 0.50, 1.00, 2.50, 5.00, and 7.00-to-1. The preferred loading of the Pt is in the range of 0.25 wt % to 5.0 wt %, with weight percentages of 0.10% and 0.05% between, such as 0.35%, 0.45%, 0.75%, 1.10%, 1.15%, 2.00%, 2.50%, 3.0%, and 4.0%.

The APR catalyst and the deoxygenation catalyst may also be different formulations. The catalysts may also be a single catalyst with both APR and deoxygenation functionality provided by the combination of the above described APR materials and deoxygenation materials.

In such event, the preferred atomic ratio of the APR catalyst to the deoxygenation catalyst is in the range of 5:1 to 1:5, such as, without limitation, 4.5:1, 4.0:1, 3.5:1, 3.0:1, 2.5:1, 2.0:1, 1.5:1, 1:1, 1:1.5, 1:2.0, 1:2.5, 1:3.0, 1:3.5, 1:4.0, 1:4.5, and any amounts between.

Similar to the deoxygenation reactions, the APR reforming temperature and pressure conditions are preferably selected to maintain at least a portion of the feedstock in the liquid phase at the reactor inlet. The reforming temperature and pressure conditions may also be selected to more favorably produce the desired products in the vapor-phase or in a mixed phase having both a liquid and vapor phase. In general, the APR reaction should be conducted at a temperature where the thermodynamics are favorable. For instance, the minimum pressure required to maintain a portion of the feedstock in the liquid phase will vary with the reaction temperature. As temperatures increase, higher pressures will generally be required to maintain the feedstock in the liquid phase. Any pressure above that required to maintain the feedstock in the liquid phase (i.e., vapor-phase) is also a suitable operating pressure. For vapor phase reactions, the reaction should be conducted at a reforming temperature where the vapor pressure of the oxygenated hydrocarbon compound is at least about 0.1 atm. (and preferably a good deal higher), and the thermodynamics of the reaction are favorable. The temperature will vary depending upon the specific oxygenated hydrocarbon compound used, but is generally in the range of from about 100° C. to 450° C., or from about 100° C. to 300° C., for reactions taking place in the vapor phase. For liquid phase reactions, the reforming temperature may be from about 80° C. to 400° C., and the reforming pressure from about 72 psig to 1300 psig.

In one embodiment, the reforming temperature is between about 100° C. and 400° C., or between about 120° C. and 300° C., or between about 200° C. and 280° C., or between about 150° C. and 270° C. The reforming pressure is preferably between about 72 and 1300 psig, or between about 72 and 1200 psig, or between about 145 and 1200 psig, or between about 200 and 725 psig, or between about 365 and 700 psig, or between about 600 and 650 psig.

In embodiments where the APR catalyst and the deoxygenation catalyst are combined into a single catalyst, or the reactions are conducted simultaneously in a single reactor with separate catalysts, the reforming temperature and deoxygenation temperature may be in the range of about 100° C. to 325° C., or about 120° C. to 300° C., or about 200° C. to 280° C., and the reforming pressure and deoxygenation pressure may be in the range of about 200 psig to 1500 psig, or about 200 psig to 1200 psig, or about 200 psig to 725 psig.

A condensed liquid phase method may also be performed using a modifier that increases the activity and/or stability of the APR catalyst system. It is preferred that the water and the oxygenated hydrocarbon are reacted at a suitable pH of from about 1.0 to 10.0, or at a pH of from about 4.0 to 10.0, including pH value increments of 0.1 and 0.05 between. Generally, the modifier is added to the feedstock solution in an amount ranging from about 0.1% to about 10% by weight as compared to the total weight of the catalyst system used, although amounts outside this range are included within the present invention.

Alkali or alkali earth salts may also be added to the feedstock solution to optimize the proportion of hydrogen in the reaction products. Examples of suitable water-soluble salts include one or more selected from the group consisting of an alkali or an alkali earth metal hydroxide, carbonate, nitrate, or chloride salt. For example, adding alkali (basic) salts to provide a pH of about pH 4.0 to about pH 10.0 can improve hydrogen selectivity of reforming reactions.

The addition of acidic compounds may also provide increased selectivity to the desired reaction products. It is preferred that the water-soluble acid is selected from the group consisting of nitrate, phosphate, sulfate, chloride salts, and mixtures thereof. If an acidic modifier is used, it is preferred that it be present in an amount sufficient to lower the pH of the aqueous feed stream to a value between about pH 1.0 and about pH 4.0. Lowering the pH of a feed stream in this manner may increase the proportion of oxygenates in the final reaction products.

In general, the reaction should be conducted under conditions where the residence time of the feedstock solution over the APR catalyst is appropriate to generate an amount of APR hydrogen sufficient to react with a second portion of the feedstock solution over the deoxygenation catalyst to provide the desired oxygenates. For example, the WHSV for the reaction may be at least about 0.1 gram of oxygenated hydrocarbon per gram of APR catalyst, and preferably between about 1.0 to 40.0 grams of oxygenated hydrocarbon per gram of APR catalyst, and more preferably between about 0.5 to 8.0 grams of oxygenated hydrocarbon per gram of APR catalyst. In terms of scaled-up production, after start-up, the APR reactor system should be process controlled so that the reactions proceed at steady-state equilibrium.

Catalyst Regeneration

During liquefaction, carbonaceous deposits build up on the heterogeneous liquefaction catalyst surface through minor side reactions of the biomass and other generated products. As these deposits accumulate, access to the catalytic sites on the surface becomes restricted and the catalyst performance declines, resulting in lower conversion and yields to desired products.

To regenerate the heterogeneous liquefaction catalyst, the biomass product stream undergoes one or more separation steps to separate the liquefaction catalyst, extractives, unreacted biomass and under-reacted biomass from the liquid portion. Various separation techniques known in the art may be used. Such techniques may include, without limitation, gravitational settling techniques, cyclone separation techniques, simulated moving bed technology, distillation, filtration, etc. In one embodiment, the biomass product stream is directed into a settling tank configured to allow a bottom portion containing solid materials (e.g., the liquefaction catalyst, extractives and unreacted or under-reacted materials) to separate from a top portion containing a significant portion of the liquid solution of oxygenated compounds and the residual or resulting gases generated in the system. A fraction of the solution of oxygenated compounds may also be maintained in the bottom portion to assist with the movement of the solid materials through additional processing steps or for recycling to the biomass slurry for use as a solvent.

The bottom portion of the biomass product stream is further apportioned by separating the liquefaction catalyst from the extractives and unreacted or under-reacted materials using a washing medium. The washing medium can be any medium capable of washing unreacted species from the catalyst and reactor system. Such washing medium may include any one of several liquid media, such as water, alcohols, ketones, or other oxygenated hydrocarbons, whether alone or in combination with any of the foregoing, and which does not include materials known to be poisons for the catalyst in use (e.g., sulfur). The washing step may include either soaking the catalyst for a period of time (e.g. 5 or more minutes), flushing with the washing medium, or a combination of both, and at a temperature that does not cause the liquid washing medium or the unreacted species to change to the gaseous phase. The washing step may also involve multiple flushing activities, including one or more initial washes with an organic solvent, followed by one or more washes with water, or vice-versa, until the liquefaction catalyst is free of extractives and other unwanted materials. In one embodiment, the temperature is maintained below about 100° C. during the washing step.

In certain applications, the liquefaction catalyst may still be in a mixture with unreacted and under-reacted biomass after washing, thereby requiring additional separation. In general, the liquefaction catalyst will tend to be heavier than the biomass and can be readily separated using various techniques, including cyclone separation, centrifugation, and gravitational settling, among others.

The liquefaction catalyst is then dried at a temperature and pressure sufficient to remove any water from the catalyst (e.g., 120° C. and at atmospheric pressure). Once dried, the temperature in the reactor is increased at a rate of about 20° C. per hour to about 60° C. per hour, and is maintained at a temperature between about 300° C. and about 500° C. Throughout the regeneration and cooling process, a gas flow of 1,000 ml/min of regenerant gas is maintained. In one embodiment, the regenerant gas is a mixture of inert gas (e.g., nitrogen) and 3% oxygen. In another embodiment, the regenerant gas includes hydrogen.

The regeneration will result in the production of a regeneration stream, the composition of which will vary depending on the regenerant gas. For example, light paraffins such as methane, ethane, and propane are emitted as a regeneration stream as the carbonaceous deposits are removed from the catalyst using hydrogen as a regenerant gas. At temperatures between about 80° C. and about 100° C., C—O and C—C linkages in the carbonaceous deposits are broken and $C_2$-$C_6$ alkanes and oxygenates are released from the catalyst and collected in a downstream phase separator or removed in the gas phase. As temperatures continue to rise toward about 500° C., C—C bond hydrogenolysis predominates. While methane makes up the largest fraction of the carbon removed at all temperatures, significant levels of larger paraffins are evolved as well. The composition of the larger paraffins gradually shifts from longer chain components, such as pentane and hexane, to shorter chain paraffins, such as ethane and methane, as the temperature increases. When a mixture of nitrogen and 3% oxygen is used as a regenerant gas, the regeneration stream will almost exclusively include CO and $CO_2$.

One method of monitoring the regeneration stream is using a gas chromatogram, such as an SRI 9610C GC with thermal conductivity and flame ionizing detectors in series using a molecular sieve column and a silica gel column in column switching arrangement for component separation. The product profile over time for a hydrogen regenerant gas suggests a typical trend of an inverse relationship between paraffin abundance and carbon number. Based on this trend, to obtain a maximum return of performance, the regeneration is continued until the methane content of the regeneration stream is below 0.3% by volume. However, a general increase in activity can also be seen with substantially greater residual paraffin content. The liquefaction catalyst is considered completely regenerated when sufficient carbonaceous deposits have been removed such that liquefaction can be resumed. This generally occurs when the methane given off during the catalyst regeneration decreases to an insignificant amount. In a preferred embodiment, the liquefaction catalyst is considered regenerated when the amount of methane in the catalyst regeneration environment is less than 4%, more preferably less than 2%, and most preferably less than 0.3%. To ensure that maximum regeneration is achieved, the liquefaction catalyst may need to be regenerated at its highest temperature for a period of up to 16 hours.

The product profile over time for an oxygen-based regenerant gas suggests a relationship between $CO_2$ abundance and catalyst regeneration. Based on this trend, to obtain a maximum return of performance, the regeneration is continued until the $CO_2$ content of the regeneration stream is below 0.1% by volume. However, a general increase in activity can also be seen with substantially greater $CO_2$ content. The liquefaction catalyst is considered completely regenerated when sufficient carbonaceous deposits have been removed such that liquefaction can be resumed. This generally occurs when the $CO_2$ given off during the catalyst regeneration decreases to an insignificant amount. In a preferred embodiment, the liquefaction catalyst is considered regenerated when the amount of $CO_2$ in the catalyst regeneration environment is less than 4%, more preferably less than 2%, and most preferably less than 0.1%. To ensure that maximum regeneration is achieved, the liquefaction catalyst may need to be regenerated at its highest temperature for a period of up to 16 hours.

The accumulation of paraffins and $CO_2$, respectively, during regeneration can be utilized to calculate the total grams of carbon removed per gram of catalysts. When the regeneration is run to maximize system performance, the amount of carbon per gram of catalyst can be utilized to determine average rate of deposit for carbonaceous species as well as provide some predictive information on the duration between regenerations assuming similar operating conditions are used.

Extractives

In addition to lignin, cellulose and hemicellulose, biomass includes ash, terpenoids, stilbenes, flavonoids, proteins, and other inorganic products not amenable to downstream conversion processes as those contemplated herein. In practicing the present invention, such materials, as well as unreacted or under reacted lignin, cellulose and hemicellulose, will often be present in the product stream as a solid material and removed as part of the catalytic washing process. Ultimately, the lignin, ash and other extractives can be purged from the system and used in other processes. For example, the lignin can be burned to provide process heat, while the proteinaceous material can be used for animal feed or as other products. The unreacted or under-reacted cellulose and hemicellulose can be recycled to the biomass slurry and processed until fully reacted.

Example 1

Figure 4:
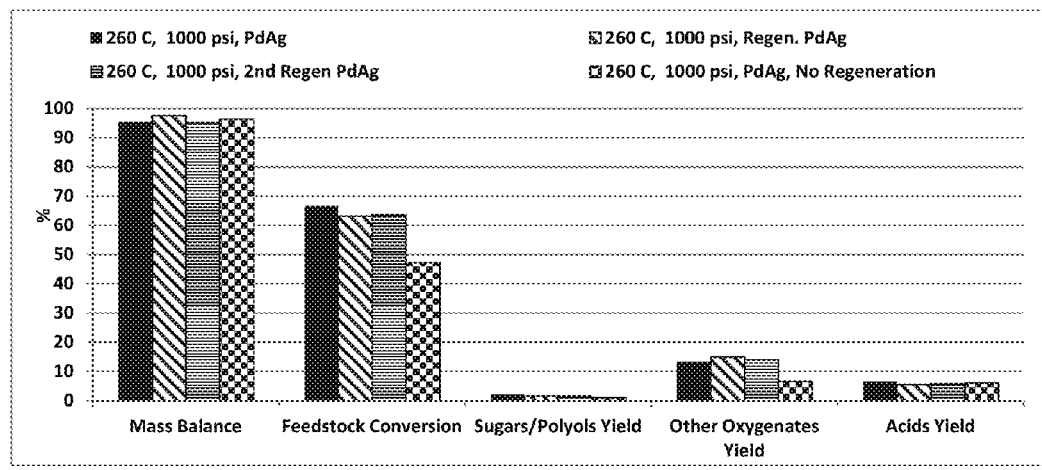
FIG. 4 is a graph illustrating the results from the liquefaction of loblolly pine in accordance with the present invention.
Figure 5:
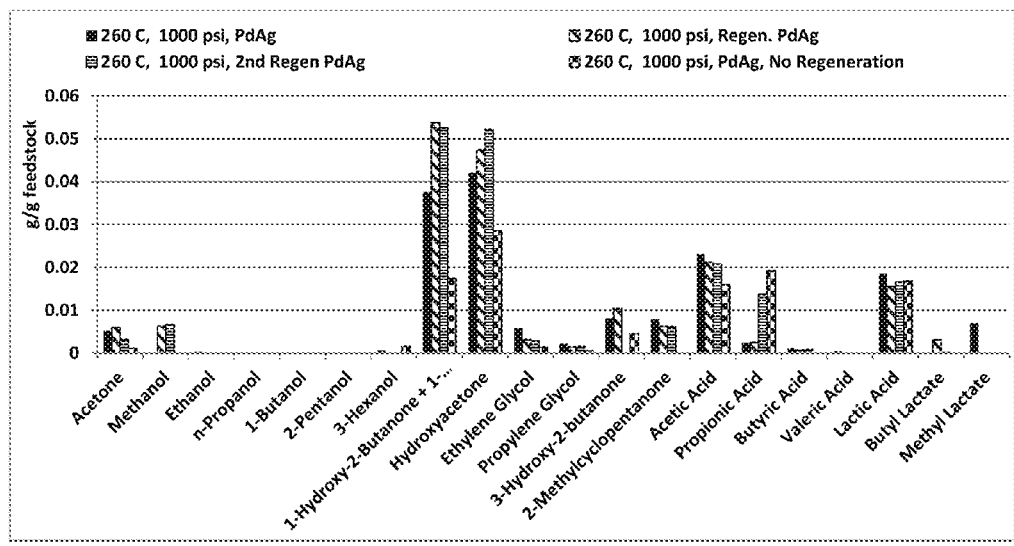
FIG. 5 is a graph illustrating the results from the liquefaction of loblolly pine using a regenerated liquefaction catalyst in accordance with the present invention.

A heterogeneous liquefaction catalyst, 2% Pd 2% Ag on a tungstated zirconia support, was used for the liquefaction of loblolly pine to determine catalyst activity and regeneration effects. Reactor conditions were 10% (w/v) loblolly pine slurry in water, 1:3 catalyst:pine, 260° C., 1000 psi $H_2$. A fresh catalyst sample was used for the liquefaction, the spent catalyst was then regenerated and used again. Regeneration included an organic solvent (acetone) wash, followed by several water washings to remove residual solvent and an oxidative regeneration. The oxidative regeneration conditions were as follows: 0.8° C. per minute ramp to 450° C. followed by a 16 hour hold at temperature, with a gas flow of 1000 ml/min $N_2$ and 3% oxygen. The spent catalyst was again collected and used once more after a second regeneration. One final run was then conducted using the spent catalyst, this time without any regeneration. Results can be seen in FIGS. 4 and 5.

For pine liquefaction, the liquefaction catalyst activity tended to remain after initial use, shown by feedstock conversion in both of the regenerated catalysts, however feedstock conversion dropped when the catalyst was not regenerated. There was a slight change in product selectivity with the regenerated catalysts producing more hydroxyketones than the fresh catalyst. However, general product distribution remained similar. A decrease in feedstock conversion, as well as a significant reduction in the production of the alcohols, ketones and hydroxyketones, was observed when using non-regenerated catalysts.

Example 2

Figure 6:
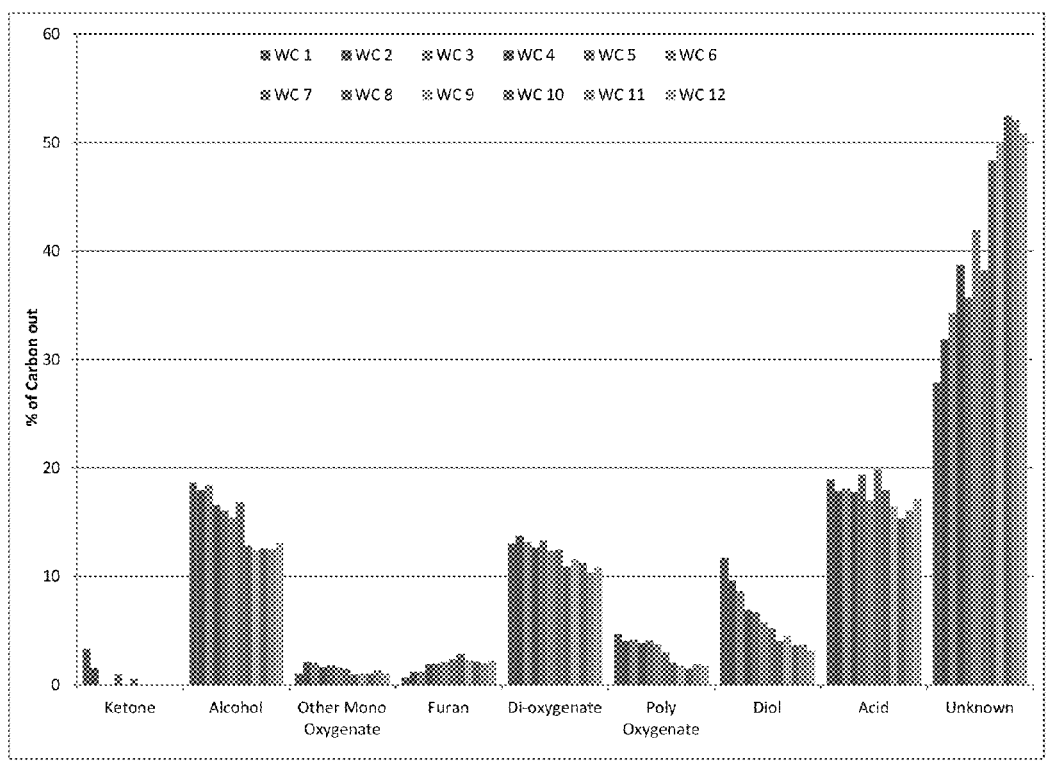
FIG. 6 is a graph illustrating the results from the liquefaction of corn cobs using a regenerated liquefaction catalyst in accordance with the present invention.

A non-precious metal liquefaction catalyst (5% Ni Ni:B (1:5)) was used for the liquefaction of corn cobs for a 3 day continuous run in a slurry reactor. Reactor conditions were 5 wt % corn cob in water, 1:3 catalyst:biomass, 260° C., 1000 psi $H_2$. Fresh catalyst was added each cycle, roughly every 10 minutes, for the first 12 hours. After 12 hours, the catalyst was recycled and fresh catalyst was added less than once per hour, or every 6 cycles. No regeneration of the catalyst occurred. The results can be seen in FIG. 6 and Table 2.

TABLE 2

| Species | grams per minute |
|---|---|
| Acetol | 0.20 |
| 1-Hexanol | 0.17 |
| Butanoic acid | 0.14 |
| Acetic acid | 0.13 |
| Ethylene glycol | 0.10 |
| Propylene glycol | 0.07 |
| Acetone | 0.04 |
| Propionic Acid | 0.04 |
| (R)-(−)-2-Pentanol | 0.03 |
| Glycerol | 0.02 |
| Xylitol | 0.02 |
| 1,2-Pentanediol | 0.02 |
| Methyl propionate | 0.02 |
| Lactic acid | 0.01 |
| Formic Acid | 0.01 |

For corn cob liquefaction, the catalyst activity remained throughout the 3 day run shown by feedstock conversion and the ability to run with such longevity. Product selectivity over the run was observed, with a decrease in alcohols and diols and an increase in unknown products.

Example 3

Figure 7:
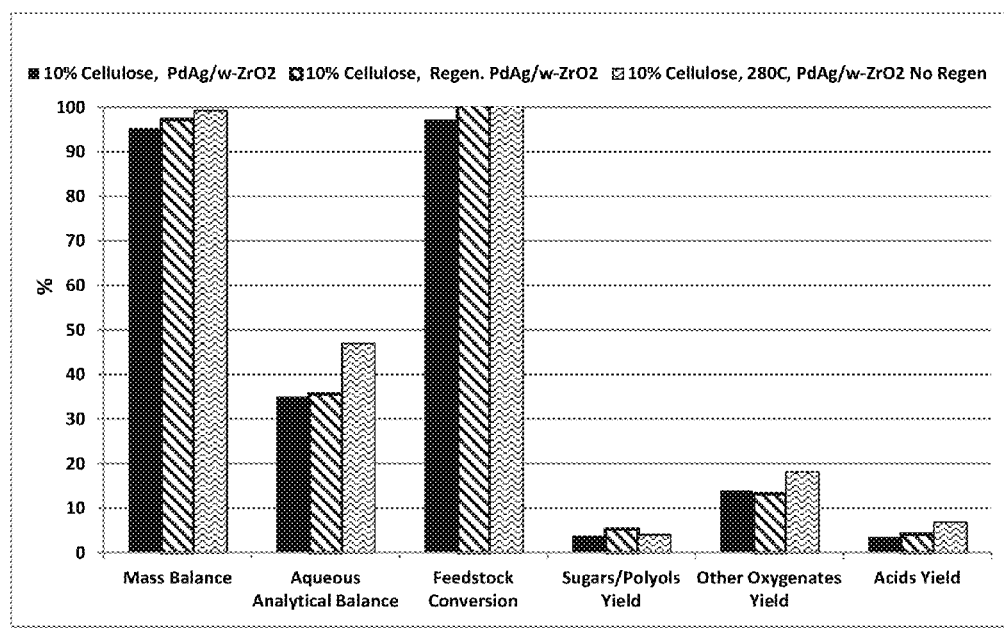
FIG. 7 is a graph illustrating the results from the liquefaction of microcrystalline cellulose using regenerated and non-regenerated liquefaction catalysts in accordance with the present invention.
Figure 8:
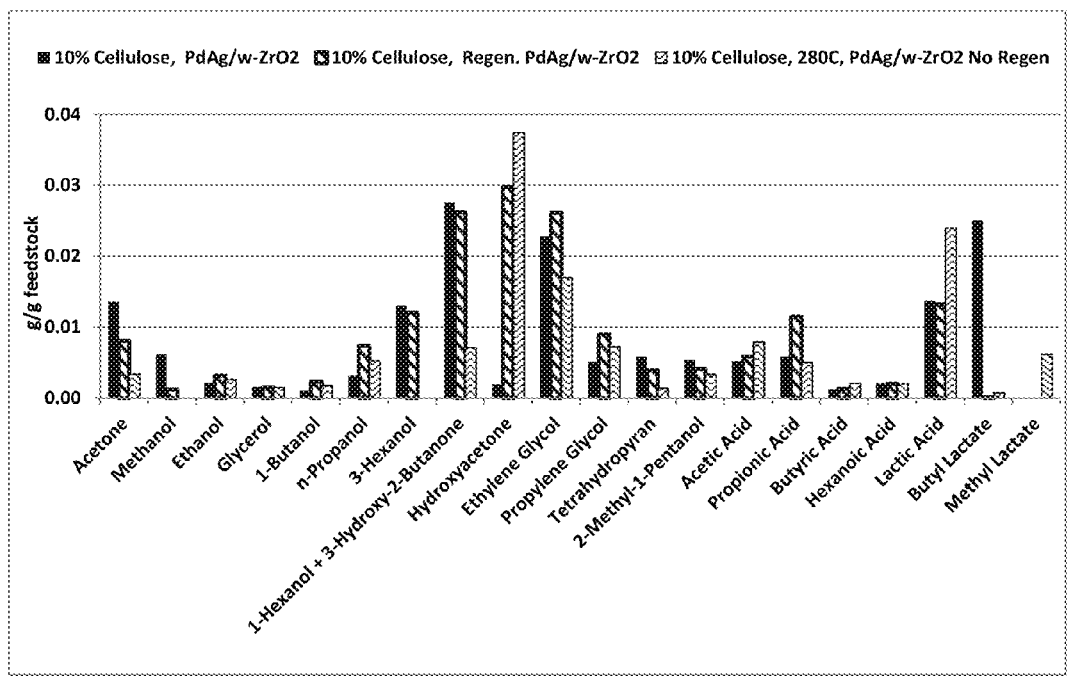
FIG. 8 is a graph illustrating the results from the liquefaction of microcrystalline cellulose using regenerated and non-regenerated liquefaction catalysts in accordance with the present invention.

A heterogeneous liquefaction catalyst, 2% Pd 2% Ag on tungstated zirconia support, was used for liquefaction of microcrystalline cellulose (MCC) to determine catalyst activity and regeneration effects. Reactor conditions were 10% (w/v) MCC slurry in water, 1:3 catalyst:biomass, 260° C., 1000 psi $H_2$. A fresh catalyst sample was used for liquefaction, then regenerated and used again. Regeneration included an organic solvent (acetone) wash, followed by several water washings to remove residual solvent and an oxidative regeneration. The oxidative regeneration conditions were as follows: 0.8° C. per minute ramp to 450° C. followed by a 16 hour hold at temperature, with a gas flow of 1000 ml/min $N_2$ and 3% oxygen. The spent catalyst was again collected and used once more, this time without any regeneration. Results can be seen in FIGS. 7 and 8.

The activity of the liquefaction catalyst tended to remain after initial use, shown by feedstock conversion in both the regenerated catalyst and non-regenerated catalyst. There was a slight change in product selectivity with the regenerated catalysts producing more hydroxyketones than the fresh catalyst. However, general product distribution remained similar. Without a regeneration of the catalyst, a significant reduction in the production of the alcohols favoring more hydroxyketones was observed.

Example 4

A heterogeneous liquefaction catalyst, 2% Pd 2% Ag on tungstated zirconia support, was used for liquefaction of loblolly pine to determine catalyst activity and regeneration effects. The loblolly pine slurry had a concentration of 10 wt % solids in water, and was reacted for a 90 minute heating period at varying temperatures of 240° C. to 300° C., and varying partial pressures of hydrogen from 1000 psi to 1450 psi. All of the runs were pre-pressurized to a level that would ensure the aqueous phase reaction of the lignocellulose.

Figure 9:
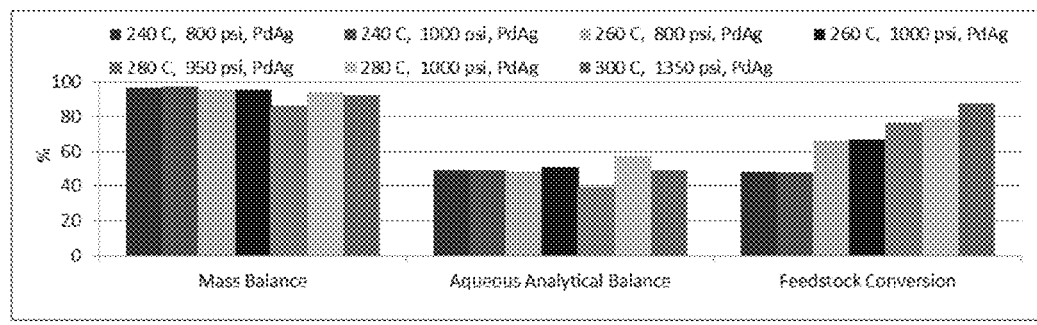
FIG. 9 is a graph illustrating the results from the liquefaction of loblolly pine using a liquefaction catalyst in accordance with the present invention.
Figure 10:
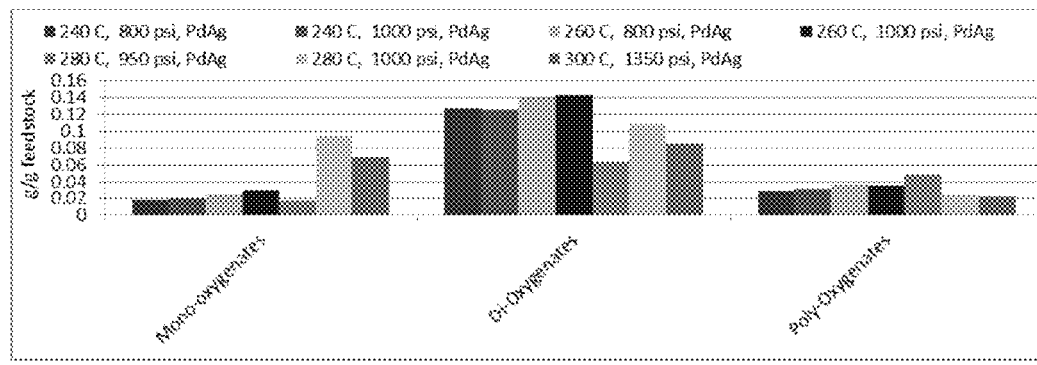
FIG. 10 is a graph illustrating the results from the liquefaction of loblolly pine using a liquefaction catalyst in accordance with the present invention.

FIGS. 9 and 10 illustrate the ability of the liquefaction catalysts to convert most of the lignocellulose to the aqueous phase and selectively to a wide range of products, many of which are highly deoxygenated. Temperature plays a large role in the conversion of feedstock, particularly to oxygenate formation, as the sugars/polyols and acids yields were relatively constant throughout the study. With the increased temperature, the feedstock was further converted, but to a greater amount of unknowns, potentially due to cyclic or phenolic type structures predicted from lignin conversion. A decrease in carbon conversion to the aqueous phase was also seen with increased reaction time, indicating greater losses to the gas phase and degradation through condensation of products on the catalyst and reactor.

Increased reaction times appear to increase feedstock conversion, but once again the conversion is to a greater number of unknown species. Oxygenate yields tend to decrease marginally at greater reaction times as well, potentially indicating more degradation with longer reaction times.

Example 5

Figure 11:
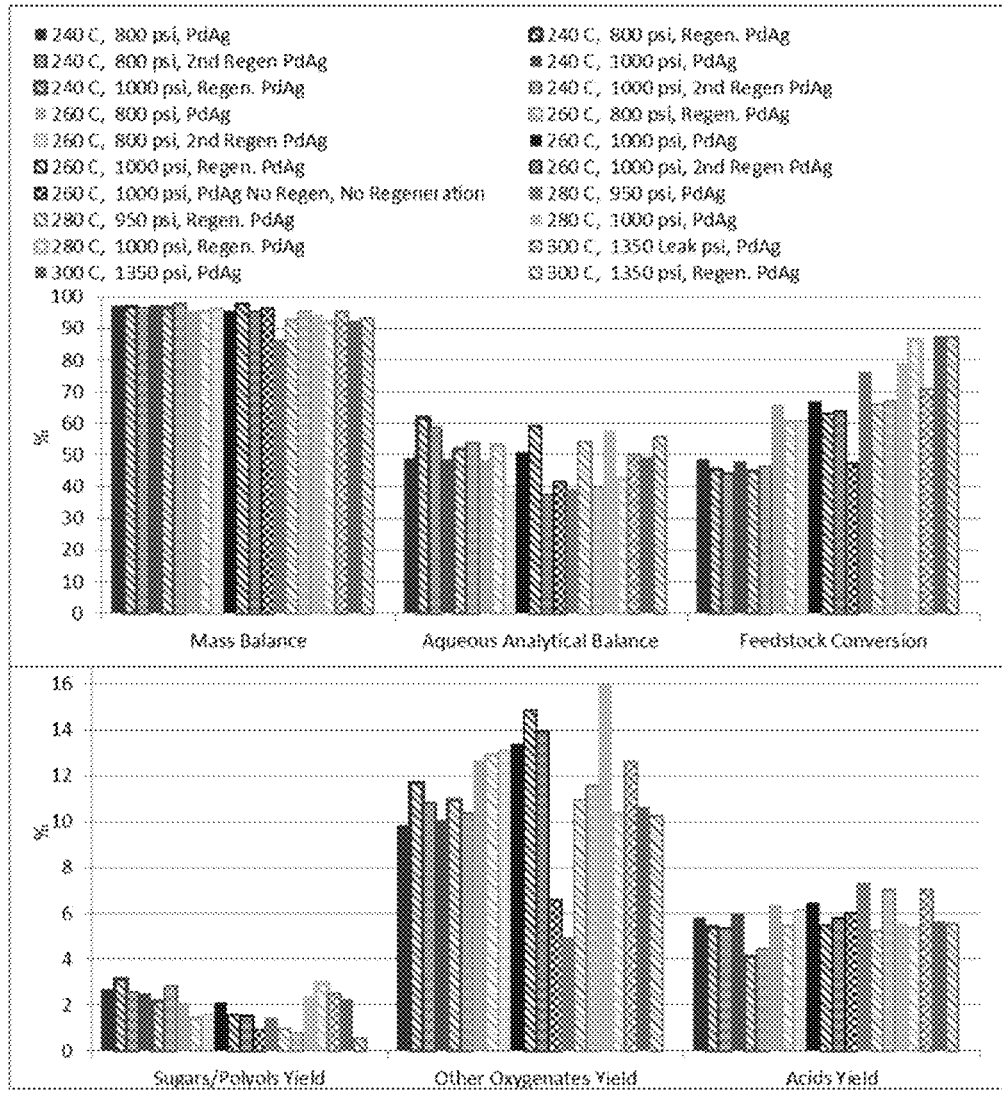
FIG. 11 is a graph illustrating the results from the liquefaction of loblolly pine using a regenerated and non-regenerated liquefaction catalyst in accordance with the present invention.

The liquefaction catalyst used in Example 4 was regenerated according to the present invention. Regeneration included an organic solvent (acetone) wash, followed by several water washings to remove residual solvent and an oxidative regeneration. The catalyst was then dried at 105° C. for 24 hours before regeneration. The oxidative regeneration conditions were as follows: 0.8° C. per minute ramp to 425° C. followed by a 24 hour hold at temperature, with a gas flow of 1000 ml/min $N_2$ and 3% oxygen. The spent catalyst was again collected and used as described in Example 4, followed by a second generation and additional processing. The results can be seen in FIG. 11.

We claim:

1. A method of converting a biomass slurry comprising water and a biomass component that is insoluble in water to lower molecular weight oxygenated hydrocarbons, the method comprising:
(a) catalytically reacting the biomass slurry with a biomass processing solvent, hydrogen, and a heterogeneous liquefaction catalyst at a liquefaction temperature and a liquefaction pressure in a reactor to produce a product stream,
wherein the product stream comprises the liquefaction catalyst, extractives and an aqueous solution comprising lower molecular weight oxygenated hydrocarbons, wherein the biomass processing solvent comprises a $C_{2+}O_{1-3}$ hydrocarbon, and wherein the biomass processing solvent is produced by catalytically reacting in the liquid or vapor phase an aqueous feedstock solution comprising water and a water-soluble oxygenated hydrocarbon comprising a $C_{2+}O_{1+}$ hydrocarbons with $H_2$ in the presence of a deoxygenation catalyst at a deoxygenation temperature and deoxygenation pressure;

(b) separating the liquefaction catalyst and extractives from the product stream to provide a liquid stream comprising lower molecular weight oxygenated hydrocarbons;

(c) washing the liquefaction catalyst in a washing medium;

(d) regenerating the liquefaction catalyst in a regenerant gas at a regenerating pressure and regenerating temperature wherein carbonaceous deposits are removed from the catalyst; and (e) reintroducing the liquefaction catalyst to the reactor.

2. The method of claim 1, wherein the water-soluble oxygenated hydrocarbon is the liquid stream.

3. The method of claim 1, the method further comprising reintroducing at least a portion of the lower molecular weight oxygenated hydrocarbons to the reactor.

4. The method of claim 1, wherein the biomass processing solvent comprises a member selected from the group consisting of an alcohol, ketone, aldehyde, cyclic ether, ester, diol, triol, hydroxy carboxylic acid, carboxylic acid, and a mixture thereof.

5. The method of claim 4, wherein the biomass processing solvent comprises a member selected from the group consisting of ethanol, n-propyl alcohol, isopropyl alcohol, butyl alcohol, pentanol, hexanol, cyclopentanol, cyclohexanol, 2-methylcyclopentanol, a hydroxyketone, a cyclic ketone, acetone, propanone, butanone, pentanone, hexanone, 2-methyl-cyclopentanone, ethylene glycol, 1,3-propanediol, propylene glycol, butanediol, pentanediol, hexanediol, methylglyoxal, butanedione, pentanedione, diketohexane, a hydroxyaldehyde, acetaldehyde, propionaldehyde, butyraldehyde, pentanal, hexanal, formic acid, acetic acid, propionic acid, butanoic acid, pentanoic acid, hexanoic acid, lactic acid, glycerol, furan, tetrahydrofuran, dihydrofuran, 2-furan methanol, 2-methyl-tetrahydrofuran, 2,5-dimethyl-tetrahydrofuran, 2-ethyl-tetrahydrofuran, 2-methyl furan, 2,5-dimethyl furan, 2-ethyl furan, hydroxylmethylfurfural, 3-hydroxytetrahydrofuran, tetrahydro-3-furanol, 5-hydroxymethyl-2 (5H)-furanone, dihydro-5-(hydroxymethyl)-2(3H)-furanone, tetrahydro-2-furoic acid, dihydro-5-(hydroxymethyl)-2(3H)-furanone, tetrahydrofurfuryl alcohol, 1-(2-furyl)ethanol, and hydroxymethyltetrahydrofurfural, isomers thereof, and combinations thereof.

6. The method of claim 2, wherein the deoxygenation catalyst comprises a support and a member selected from the group consisting of Re, Cu, Fe, Ru, Ir, Co, Rh, Pt, Pd, Ni, W, Os, Mo, Ag, Au, an alloy thereof, and a combination thereof.

7. The method of claim 2, wherein the deoxygenation catalyst further comprises a member selected from the group consisting of Mn, Cr, Mo, W, V, Nb, Ta, Ti, Zr, Y, La, Sc, Zn, Cd, Ag, Au, Sn, Ge, P, Al, Ga, In, Tl, an alloy thereof, and a combination thereof.

8. The method of claim 6, wherein the support comprises a member selected from group consisting of a carbon, silica, alumina, zirconia, titania, vanadia, heteropolyacid, kieselguhr, hydroxyapatite, chromia, zeolite, and mixtures thereof.

9. The method of claim 8, wherein the support is selected from the group consisting of tungstated zirconia, tungsten modified zirconia, tungsten modified alpha-alumina, or tungsten modified theta alumina.

10. The method of claim 1, wherein the deoxygenation temperature is in the range of about 120° C. to 325° C., and the deoxygenation pressure is at least 0.1 atmosphere.

11. The method of claim 1, wherein the deoxygenation temperature is greater than 120° C., or 150° C., or 180° C., or 200° C., and less than 325° C., or 300° C., or 280° C., or 260° C., or 240° C., or 220° C.

12. The method of claim 1, wherein the deoxygenation pressure is greater than 200 psig, or 365 psig, or 500 psig or 600 psig, and less than 2500 psig, or 2250 psig, or 2000 psig, or 1800 psig, or 1500 psig, or 1200 psig, or 1000 psig, or 725 psig.

13. The method of claim 1, wherein the biomass component is selected from the group consisting of lignin, cellulose, and hemicellulose.

14. The method of claim 1, wherein biomass component comprises lignocellulose.

15. The method of claim 1, wherein the biomass component is selected from the group consisting of an agricultural residue, a wood material, municipal solid waste, and an energy crop.

16. The method of claim 1, wherein the biomass component is selected from the group consisting of corn stover, straw, seed hulls, sugarcane leavings, bagasse, nutshells, cotton gin trash, manure, wood, bark, sawdust, timber slash, mill scrap, recycled paper, waste paper, yard clippings, poplars, willows, switch grass, miscanthus, sorghum, alfalfa, prairie bluestream, corn, and soybean.

17. The method of claim 1, wherein the lower molecular weight oxygenated hydrocarbons or the water-soluble oxygenated hydrocarbon comprise a member selected from the group consisting of a starch, a carbohydrate, a polysaccharide, a disaccharide, a monosaccharide, a sugar, a sugar alcohol, an alditol, an organic acid, a phenol, a cresol, ethanediol, ethanedione, acetic acid, propanol, propanediol, propionic acid, glycerol, glyceraldehyde, dihydroxyacetone, lactic acid, pyruvic acid, malonic acid, a butanediol, butanoic acid, an aldotetrose, tartaric acid, an aldopentose, an aldohexose, a ketotetrose, a ketopentose, a ketohexose, a hemicellulose, a cellulosic derivative, a lignocellulosic derivative, a polyol, and combinations thereof.

18. A method of converting a biomass slurry comprising water and a biomass component that is insoluble in water to lower molecular weight oxygenated hydrocarbons, the method comprising:

catalytically reacting the biomass slurry with hydrogen, and a heterogeneous liquefaction catalyst at a liquefaction temperature and a liquefaction pressure to produce a product stream comprising the liquefaction catalyst, extractives and an aqueous solution comprising lower molecular weight oxygenated hydrocarbons.

19. The method of claim 18, wherein the step of catalytically reacting the biomass slurry further comprises contacting the biomass slurry with a biomass processing solvent.

20. A method of converting a biomass slurry comprising water and a biomass component that is insoluble in water to lower molecular weight oxygenated hydrocarbons, the method comprising:

(a) catalytically reacting in the liquid or vapor phase an aqueous feedstock solution with $H_2$ in the presence of a deoxygenation catalyst at a deoxygenation temperature and deoxygenation pressure to produce a biomass processing solvent, wherein the aqueous feedstock comprises water and a water-soluble oxygenated hydrocarbon, wherein the water-soluble oxygenated hydrocarbon comprises a $C_{2+}O_{1+}$ hydrocarbon, and wherein the biomass processing solvent comprises a $C_{2+}O_{1-3}$ hydrocarbon; and (b) catalytically reacting the biomass slurry with a biomass processing solvent, hydrogen, and a heterogeneous liquefaction catalyst at a liquefaction temperature and a liquefaction pressure in a reactor to produce a product stream, wherein the product stream comprises the liquefaction catalyst, extractives and an aqueous solution comprising lower molecular weight oxygenated hydrocarbons.

* * * * *